(12) United States Patent
Yi et al.

(10) Patent No.: US 7,279,497 B2
(45) Date of Patent: Oct. 9, 2007

(54) BENZOPYRAN DERIVATIVES SUBSTITUTED WITH SECONDARY AMINES INCLUDING IMIDAZOLE, THEIR PREPARATION AND PHARMACEUTICAL COMPOSITIONS CONTAINING THEM

(75) Inventors: Kyu Yang Yi, Taejeon-si (KR); Sun Kyung Lee, Taejeon-si (KR); Sung-Eun Yoo, Gongju-si (KR); Jee Hee Suh, Taejeon-si (KR); Nak Jeong Kim, Taejeon-si (KR); Sun Kyung Hwang, Taejeon-si (KR); Byung-Ho Lee, Taejeon-si (KR); Ho Won Seo, Taejeon-si (KR); Chong Ock Lee, Taejeon-si (KR); Sang-Un Choi, Taejeon-si (KR)

(73) Assignee: Korea Research Institute of Chemical Technology, Taejeon-si (KR)

( * ) Notice: Subject to any disclaimer, the term of this patent is extended or adjusted under 35 U.S.C. 154(b) by 397 days.

(21) Appl. No.: 10/523,015

(22) PCT Filed: Jul. 30, 2003

(86) PCT No.: PCT/KR03/01534

§ 371 (c)(1),
(2), (4) Date: Feb. 2, 2005

(87) PCT Pub. No.: WO2004/014898

PCT Pub. Date: Feb. 19, 2004

(65) Prior Publication Data

US 2005/0267188 A1 Dec. 1, 2005

(30) Foreign Application Priority Data

Aug. 9, 2002 (KR) ............. 10-2002-0047189

(51) Int. Cl.
*A61K 31/4164* (2006.01)
*C07D 233/54* (2006.01)

(52) U.S. Cl. ............... 514/397; 548/300.1; 548/311.1; 548/311.4; 514/385; 514/396

(58) Field of Classification Search ............ 548/300.1, 548/311.1, 311.4; 514/385, 396, 397
See application file for complete search history.

(56) References Cited

U.S. PATENT DOCUMENTS

| 5,629,429 A | 5/1997 | Kronenthal et al. |
| 5,837,702 A | 11/1998 | Rovnyak et al. |
| 5,869,478 A * | 2/1999 | Ding et al. ............ 514/217.03 |
| 6,521,617 B2 * | 2/2003 | Marban et al. .......... 514/223.2 |

FOREIGN PATENT DOCUMENTS

EP 0 648 758 A1 4/1995

OTHER PUBLICATIONS

Grover, G.J., et al., "Pharmacologic Characterization of BMS-191095, a Mitochondrial $K_{ATP}$ Opener with No Peripheral Vasodilator or Cardiac Action Potential Shortening Activity", *The Journal of Pharmacology and Experimental Therapeutics*, vol. 297, No. 3, pp. 1184-1192, (2001).

Ding, C.Z., et al., "Cardio selective Antiischemic ATP-Sensitive Potassium Channel ($K_{ATP}$) Openers. 6. Effect of Modifications at C6 of Benzopyranyl Cyanoguanidines", *Journal of Medicinal Chemistry*, vol. 42, No. 18, pp. 3711-3717, (1999).

Rovnyak, G.C., et al., "Cardio selective Antiischemic ATP-Sensitive Potassium Channel ($K_{ATP}$) Openers. 5. Identification of 4-(N-Aryl)-Substituted Benzopyran Derivatives with High Selectivity", *Journal of Medicinal Chemistry*, vol. 40, No. 1, pp. 24-34, (1997).

* cited by examiner

*Primary Examiner*—Golam M. M. Shameem
(74) *Attorney, Agent, or Firm*—Gary M. Nath; Joshua B. Goldberg; Tanya E. Harkins

(57) ABSTRACT

The present invention relates to benzopyran derivatives substituted with secondary amines including imidazole, their preparation, and pharmaceutical compositions containing them. The present invention is pharmacologically useful for the treatment of cancer, rheumatoid arthritis, and diabetic retinopathies through anti-angiogenic properties, and also pharmacologically useful in the protection of heart and neuronal cells against ischemia-reperfusion injury or preserving organs.

5 Claims, No Drawings

BENZOPYRAN DERIVATIVES SUBSTITUTED WITH SECONDARY AMINES INCLUDING IMIDAZOLE, THEIR PREPARATION AND PHARMACEUTICAL COMPOSITIONS CONTAINING THEM

BACKGROUND OF THE INVENTION

1. Field of the Invention

The present invention relates to novel benzopyran derivatives substituted with secondary amines including imidazole of formula 1. It also relates to process for preparing the novel compounds and pharmaceutical formulations comprising one or more of the compounds as an active ingredient.

The present invention also relates to pharmaceutical use of the benzopyran derivatives substituted with secondary amines including imidazole. In particular, the present invention is pharmacologically useful in the treatment of cancer, rheumatoid arthritis, and diabetic retinopathies through anti-angiogenic properties, and also pharmacologically useful for the protection of heart, neuronal cells, brain injury, organs for preservation or in major cardiovascular surgery against ischemia-reperfusion injury or oxidative stress.

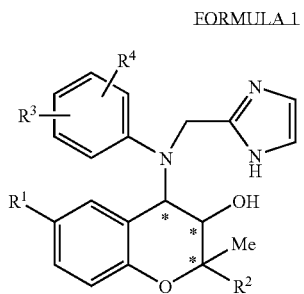

FORMULA 1

Wherein $R^1$, $R^2$, $R^3$, $R^4$ and * are each defined in specification.

2. Description of the Prior Art

The ratio of cancer in human diseases is being gradually increased despite the considerable research has been devoted to the whole area of cancer. Since the 1970s discovery by J. Folkman that angiogenesis, the formation of new blood vessels from preexisting vessels, is implicated in tumor growth, anti-angiogenics have been identified as one of the most promising and innovative drug classes.

Traditional chemotherapeutics destroy tumor cell populations by chemical poisoning of cancer cells during their productive cycles, which affect normal cells as well as tumor cells resulting in serious side effects. Therefore, the research on the development of anti-angiogenic agents, which inhibit the formation of new blood vessels to provide oxygen and nutrients, and to provide a way to metastasize to distant organs, is considered as one of the novel approaches for the anti-cancer therapies.

While angiogenesis normally occurs in adults only in the specific conditions such as wound healing and inflammation, angiogenesis is recognized as the core process for growth and metastasis of solid tumors because solid tumors could only grow to 1-2 mm without developing a blood supply (Folkman, J. et al., *J. Biol. Chem.* 267: 10931-10934 (1992)). In normal conditions the angiogenic process is under tight regulation of stimulatory and inhibitory factors. Under certain pathological conditions such as the growth of solid tumors, rheumatoid arthritis, psoriasis, complications of AIDS, and diabetic retinopathy, angiogenesis occurs in a less controlled manner (Forkman, J., Klagsbrun. M. *Science* 235: 442-447 (1987). Angiogenesis includes a series of processes such as the migration, proliferation and differentiation of endothelial cells, and is an important prerequisite for the growth and metastasis of cancers. In details because the growing tumor cells require the formation of blood vessels from host cells, angiogenesis promoters derived from tumors stimulate to induce the angiogenesis into the tumor mass. Afterwards, the blood vessels formed around the malignant tumors facilitate to metastasize the tumor cells to other sites. Therefore, the inhibition of angiogenesis leads to the prevention of the growth and metastasis of cancers. As one of the important research areas for the developing of anti-cancer drugs, extensive attention is paid to the finding of angiogenesis inducers and angiogenesis inhibitors and the revealing of their working mechanisms.

Because angiogenesis is a complex process with multiple, sequential and independent steps, it creates many potential targets for inhibition, including inhibition of angiogenesis inducers' production, inhibition of the binding of angiogenesis inducers to their receptors, inhibition of basal membrane degradation, inhibition of endothelial proliferation and migration, inhibition of capillary tube formation, and inhibition of basal membranes' syntheses and migration, etc. Thus far, proteins such as prostamine and tumor necrotic factors, polysaccharides, antibiotics, various steroid derivatives, polycataions, and polyanions have been found to be able to play roles as angiogenesis inhibitors. In particular, hydrocortisone exhibits anti-angiogenetic activity by cotreatment with heparin (Lee, A. et al., *Science* 221: 1185-1187 (1983); Crum, R. et al., *Science* 230: 1375-1378 (1985)). Recently Astra Zeneca's Iressa was launched for non small cell lung carcinoma, and several anti-angiogenic agents are currently in clinical trials. Neovastat, Tarceva, CAI and Thalomid are under phase III clinical trials with some positive results.

Ischemic heart diseases usually occur as a result of myocardial ischemia, when the oxygen supply is significantly decreased compared to the oxygen demand due to the imbalance between them. In most cases, a coronary artery disorder was found to be a main reason of the ischemic heart diseases. If the inner diameter of coronary artery becomes narrow, the blood supply, resulting in oxygen supply, becomes insufficient, which can cause angina pectoris, myocardial infarction, acute cardioplegia, arrhythmia, and so on (G. J. Grover, *Can. J. Physiol.* 75, 309 (1997); G. D. Lopaschuk et al., *Science & Medicine* 42 (1997)). Because ischemic heart diseases are also caused by other complex factors besides coronary artery disorders, drug therapy as well as operational method such as percutaneous transluminal coronary angioplasty (PTCA) is required for its treatment. For that purpose, several drugs are being used, including anti-thrombotic agents, arteriosclerosis, curatives, especially beta blockers, nitrate, calcium antagonists such as nifedipin, thromobolytics, aspirin, and angiotensin converting enzyme (ACE) inhibitors.

Differently from conventional potassium channel openers, the benzopyranyl anilinomethylimidazole compound (BMS-191095), has been reported to act selectively on ATP-sensitive potassium channels ($K_{ATP}$) located in the heart (K. S. Atwal et al., *J. Mde. Chem.* 36, 3971 (1993); K. S. Atwal et al., *J. Me. Chem.* 38, 1966 (1995)). The BMS 191095 compound was found to protect ischemic hearts without a significant lowering of blood pressure, which gives the prospects for novel drug development as a cardioprotectant.

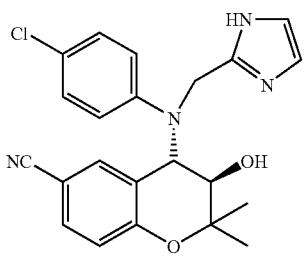

BMS-191095

Damage or death of neurons is known to be a main cause for various neurological disorders such as stroke, head trauma, Alzheimer's disease, Parkinson's disease, infant asphyxia, glaucoma and daiabetic neuropathy, etc. (G. J. Zoppo et al., *Drugs* 54, 9(1997); I. Sziraki et al., *Neurosci.* 85, 110(1998)). Neurons are damaged by various factors and typically by increases in iron concentration, reactive oxygen species, and peroxidants within neurons (M. P. Mattson et al., *Methods Cell Biol.* 46; 187 (1995); Y. Goodman et al., *Brain Res.* 706, 328 (1996)).

The intensive research on the development of compounds with the above-mentioned pharmacological efficacies by the inventors, found that the benzopyran derivatives substituted with secondary amines including imidazole represented by the formula 1. The compounds exhibit various pharmacological efficacies, including suppression of angiogenesis, in vivo anti-cancer activity, cardioprotection against ischemia-reperfusion injury, neuroprotective activity, prevention of lipid peroxidation and reactive oxygen species formation. Thus the compound of the present invention can be useful in the prevention and treatment of various diseases related to angiogenesis such as cancers, rheumatoid arthritis, and diabetic retinopathy; neuronal damage such as infant asphyxia, glaucoma, diabetic neuropathy and head trauma; oxygen free radical-related disease such as neurodegenerative diseases and atherosclerosis; and diseases related to cardiovascular system such as myocardial infarction, congestive heart failure, and angina pectoris.

DETAILED DESCRIPTION OF THE INVENTION

The present invention provides benzopyran derivatives substituted with secondary amines including imidazole by the following formula 1 and their pharmaceutically acceptable salts.

FORMULA 1

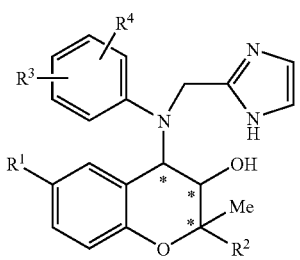

Wherein
$R^1$ represents H, CN, $NO_2$ or $NH_2$,
$R^2$ represents $CH_3$,

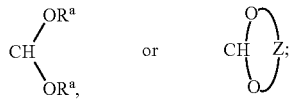

$R^a$ represents straight or branched alkyl group of $C_1$-$C_4$; and Z is straight or branched alkyl group of $C_2$-$C_6$, $R^3$ and $R^4$ are independent each other and represent H, Cl, Br, F, alkyl group of $C_1$-$C_3$, $OR^b$, $CF_3$, $QCF_3$, $NO_2$, or $CO_2R^b$; $R^b$ represents H or alkyl group of $C_1$-$C_3$, and * represents the chiral center.

The present invention includes all the solvates and hydrates which can be prepared from benzopyran derivatives substituted with secondary amines including imidazole of formula 1 in addition to benzopyran derivatives substituted with secondary amines including imidazole of formula 1 and their pharmaceutically acceptable salts.

The present invention includes all the separate stereochemical isomers, i.e. diastereomerically pure or enantiomerically pure compounds which have one or more chiral centers at 2, 3 and 4-positions, in addition to the racemic mixtures or diastereomer mixtures of benzopyran derivatives substituted with secondary amines including imidazole of formula 1.

In case of having three chiral centers at 2, 3 and 4-positions, the 3,4-dihydrobenzopyran derivatives according to the present invention are represented by the optical isomers such as ($I_1$), ($I_2$), ($I_3$) and ($I_4$). (See the following formula 2).

FORMULA 2

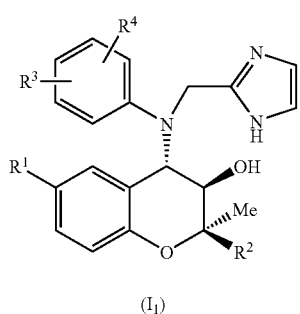

($I_1$)

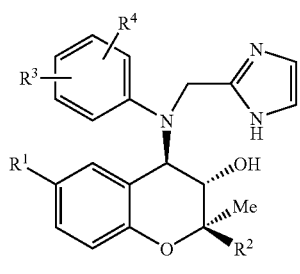

($I_2$)

-continued

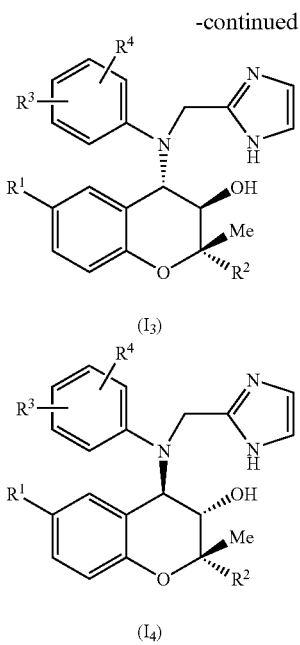

(I₃)

(I₄)

Wherein R¹, R², R³ and R⁴ are defined as above.

In particular, the preferable compounds of the present invention are:

1) (2S,3S,4R)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran;
2) (2S,3R,4S)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran;
3) (2R,3R,4S)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran;
4) (2R,3S,4R)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran;
5) (2S,3S,4R)-3,4-dihydro-2-dimethoxymethyl-3-hydroxy-2-methyl-6-nitro-4-[N-(4-trifluoromethylphenyl)-N-(1H-imidazol-2-ylmethyl)amino]-2H-1-benzopyran;
6) (2S,3S,4R)-3,4-dihydro-2-dimethoxymethyl-3-hydroxy-2-methyl-6-nitro-4-[N-(4-methoxyphenyl)-N-(1H-imidazol-2-ylmethyl)amino]-2H-1-benzopyran;
7) (2S,3S,4R)-3,4-dihydro-2-dimethoxymethyl-3-hydroxy-2-methyl-6-nitro-4-[N-(4-trifluoromethoxyphenyl)-N-(1H-imidazol-2-ylmethyl)amino]-2H-1-benzopyran;
8) (2S,3S,4R)-3,4-dihydro-2-dimethoxymethyl-3-hydroxy-2-methyl-6-nitro-4-[N-(4-bromophenyl)-N-(1H-imidazol-2-ylmethyl)amino]-2H-1-benzopyran;
9) (2S,3S,4R)-3,4-dihydro-2-dimethoxymethyl-3-hydroxy-2-methyl-6-nitro-4-[N-(2,4-dimethylphenyl)-N-(1H-imidazol-2-ylmethyl)amino]-2H-1-benzopyran;
10) (2S,3S,4R)-3,4-dihydro-2-dimethoxymethyl-3-hydroxy-2-methyl-6-nitro-4-[N-(2-isopropylphenyl)-N-(1H-imidazol-2-ylmethyl)amino]-2H-1-benzopyran;
11) (2S,3S,4R)-3,4-dihydro-2-dimethoxymethyl-3-hydroxy-2-methyl-6-nitro-4-[N-(2,3-dimethylphenyl)-N-(1H-imidazol-2-ylmethyl)amino]-2H-1-benzopyran;
12) (2R,3R,4S)-3,4-dihydro-2-dimethoxymethyl-3-hydroxy-2-methyl-6-nitro-4-[N-(2,3-dimethylphenyl)-N-(1H-imidazol-2-ylmethyl)amino]-2H-1-benzopyran;
13) (2R,3R,4S)-3,4-dihydro-2-dimethoxymethyl-3-hydroxy-2-methyl-6-nitro-4-[N-(4-bromophenyl)-N-(1H-imidazol-2-ylmethyl)amino]-2H-1-benzopyran;
14) (2R,3R,4S)-3,4-dihydro-2-dimethoxymethyl-3-hydroxy-2-methyl-6-nitro-4-[N-(4-methoxyphenyl)-N-(1H-imidazol-2-ylmethyl)amino]-2H-1-benzopyran;
15) (2S,3S,4R)-3,4-dihydro-2-dimethoxymethyl-3-hydroxy-2-methyl-6-nitro-4-[N-(4-fluorophenyl)-N-(1H-imidazol-2-ylmethyl)amino]-2H-1-benzopyran;
16) (2S,3S,4R)-3,4-dihydro-2-dimethoxymethyl-3-hydroxy-2-methyl-6-nitro-4-[N-(2-methoxyphenyl)-N-(1H-imidazol-2-ylmethyl)amino]-2H-1-benzopyran;
17) (2R,3R,4S)-3,4-dihydro-2-dimethoxymethyl-3-hydroxy-2-methyl-6-nitro-4-[N-(2-isopropylphenyl)-N-(1H-imidazol-2-ylmethyl)amino]-2H-1-benzopyran;
18) (2R,3R,4S)-3,4-dihydro-2-dimethoxymethyl-3-hydroxy-2-methyl-6-nitro-4-[N-(2-methoxyphenyl)-N-(1H-imidazol-2-ylmethyl)amino]-2H-1-benzopyran;
19) (2R,3R,4S)-3,4-dihydro-2-dimethoxymethyl-3-hydroxy-2-methyl-6-nitro-4-[N-(3-chlorophenyl)-N-(1H-imidazol-2-ylmethyl)amino]-2H-1-benzopyran;
20) (2S,3S,4R)-3,4-dihydro-2-dimethoxymethyl-3-hydroxy-2-methyl-6-nitro-4-[N-(3-chlorophenyl)-N-(1H-imidazol-2-ylmethyl)amino]-2H-1-benzopyran;
21) (2R,3R,4S)-3,4-dihydro-2-dimethoxymethyl-3-hydroxy-2-methyl-6-nitro-4-[N-(4-trifluoromethoxyphenyl)-N-(1H-imidazol-2-ylmethyl)amino]-2H-1-benzopyran;
22) (2S,3S,4R)-6-cyano-3,4-dihydro-2-dimethoxymethyl-3-hydroxy-2-methyl-4-[N-(4-chlorophenyl)-N-(1H-imidazol-2-ylmethyl)amino]-2H-1-benzopyran;
23) (2R,3R,4S)-6-amino-3,4-dihydro-2-dimethoxymethyl-3-hydroxy-2-methyl-4-[N-(4-chlorophenyl)-N-(1H-imidazol-2-ylmethyl)amino]-2H-1-benzopyran;
24) (2S,3S,4R)-6-amino-3,4-dihydro-2-dimethoxymethyl-3-hydroxy-2-methyl-4-[N-(4-chlorophenyl)-N-(1H-imidazol-2-ylmethyl)amino]-2H-1-benzopyran;
25) (2S,3S,4R)-6-amino-3,4-dihydro-2-dimethoxymethyl-3-hydroxy-2-methyl-4-[N-(4-trifluoromethylphenyl)-N-(1H-imidazol-2-ylmethyl)amino]-2H-1-benzopyran;
26) (2R,3R,4S)-6-amino-3,4-dihydro-2-dimethoxymethyl-3-hydroxy-2-methyl-4-[N-(4-trifluoromethoxyphenyl)-N-(1H-imidazol-2-ylmethyl)amino]-2H-1-benzopyran;
27) (2R,3R,4S)-6-amino-3,4-dihydro-2-dimethoxymethyl-3-hydroxy-2-methyl-4-[N-(2,3-dimethylphenyl)-N-(1H-imidazol-2-ylmethyl)amino]-2H-1-benzopyran;
28) (2R,3R,4S)-6-amino-3,4-dihydro-2-dimethoxymethyl-3-hydroxy-2-methyl-4-[N-(4-methoxyphenyl)-N-(1H-imidazol-2-ylmethyl)amino]-2H-1-benzopyran;
29) (2R,3R,4S)-6-amino-3,4-dihydro-2-dimethoxymethyl-3-hydroxy-2-methyl-4-[N-(4-bromophenyl)-N-(1H-imidazol-2-ylmethyl)amino]-2H-1-benzopyran;
30) (2S,3S,4R)-6-amino-3,4-dihydro-2-dimethoxymethyl-3-hydroxy-2-methyl-4-[N-(2,3-dimethylphenyl)-N-(1H-imidazol-2-ylmethyl)amino]-2H-1-benzopyran;
31) (2S,3S,4R)-6-amino-3,4-dihydro-2-dimethoxymethyl-3-hydroxy-2-methyl-4-[N-(2-methoxyphenyl)-N-(1H-imidazol-2-ylmethyl)amino]-2H-1-benzopyran;
32) (2S,3S,4R)-6-amino-3,4-dihydro-2-dimethoxymethyl-3-hydroxy-2-methyl-4-[N-(4-methoxyphenyl)-N-(1H-imidazol-2-ylmethyl)amino]-2H-1-benzopyran;
33) (2S,3S,4R)-6-amino-3,4-dihydro-2-dimethoxymethyl-3-hydroxy-2-methyl-4-[N-(2,4-dimethylphenyl)-N-(1H-imidazol-2-ylmethyl)amino]-2H-1-benzopyran;
34) (2S,3S,4R)-6-amino-3,4-dihydro-2-dimethoxymethyl-3-hydroxy-2-methyl-4-[N-(2-isopropylphenyl)-N-(1H-imidazol-2-ylmethyl)amino]-2H-1-benzopyran;

35) (2S,3S,4R)-6-amino-3,4-dihydro-2-dimethoxymethyl-3-hydroxy-2-methyl-4-[N-(4-trifluoromethoxyphenyl)-N-(1H-imidazol-2-ylmethyl)amino]-2H-1-benzopyran;

36) (2S,3S,4R)-6-amino-3,4-dihydro-2-dimethoxymethyl-3-hydroxy-2-methyl-4-[N-(4-bromophenyl)-N-(1H-imidazol-2-ylmethyl)amino]-2H-1-benzopyran; and 37) (2S,3S,4R)-6-amino-3,4-dihydro-2-dimethoxymethyl-3-hydroxy-2-methyl-4-[N-(4-fluorophenyl)-N-(1H-imidazol-2-ylmethyl)amino]-2H-1-benzopyran.

The compounds of formula 1 may be used as pharmaceutically acceptable salts derived from pharmaceutically or physiologically acceptable free acids. These salts include but are not limited to the following: salts with inorganic acids such as hydrochloric acid, hydrobromic acid, sulfuric acid, sulfonic acid, phosphoric acid, etc. and organic acids such as citric acid, acetic acid, maleic acid, fumaric acid, gluconic acid, methanesulfonic acid, glycolic acid, succinic acid, tartaric acid, 4-toluenesulfonic acid, galacturonic acid, embonic acid, glutamic acid, aspartic acid, etc.

The acid salts of the compounds according to the present invention can be prepared in the customary manner, for example by dissolving the compound of formula 1 in excess aqueous acid and precipitating the salt with a water-miscible organic solvent, such as methanol, ethanol, acetone or acetonitrile. It is also possible to prepare by heating equivalent amounts of the compound of formula 1 and an acid in water or an alcohol, such as glycol monomethyl ether, and then evaporating the mixture to dryness or filtering off the precipitated salt with suction.

In addition, the present invention provides processes for preparing of the benzopyran derivatives substituted with secondary amines including imidazole of formula 1.

In particular, the present invention provides processes for preparing of the benzopyran derivatives substituted with secondary amines including imidazole of formula 1 by the reaction of the compound of formula II and the compound of formula III in the presence of metal salt as represented in the following scheme 1.

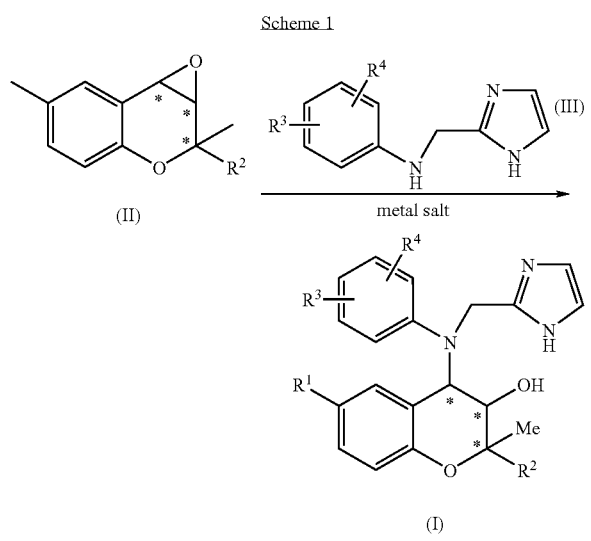

Wherein $R^1$, $R^2$, $R^3$, $R^4$, * and n are each defined as above.

The derivatives of formula 1 can be prepared separately as an optically active isomer by using the corresponding optical isomer as a starting material.

In case of using a racemic mixture as a starting material, the derivatives of formula 1 are prepared as a racemic mixture, and then the racemic mixture is separated into each optical isomers. The optical isomers can be separated by common chiral column chromatography or recrystallization.

The compounds of formula 1 can be synthesized using the reactions and techniques described herein below. The reactions are performed in a solvent appropriate to the reagents and materials employed and suitable for the transformation being effected.

I. Preparation of Starting Materials (1) Preparation of epoxide compounds (II)

Epoxide compounds ($II_1$) and epoxide compounds ($II_2$) can be prepared from the olefin compound ($IV_1$) and epoxide compounds ($II_3$) and epoxide compounds ($II_4$) can be prepared from the olefin Compound ($IV_2$) as represented by the following scheme 2, by the method disclosed in KR Pat. Appln. No. 2000-60467 which was axquired by the present inventors.

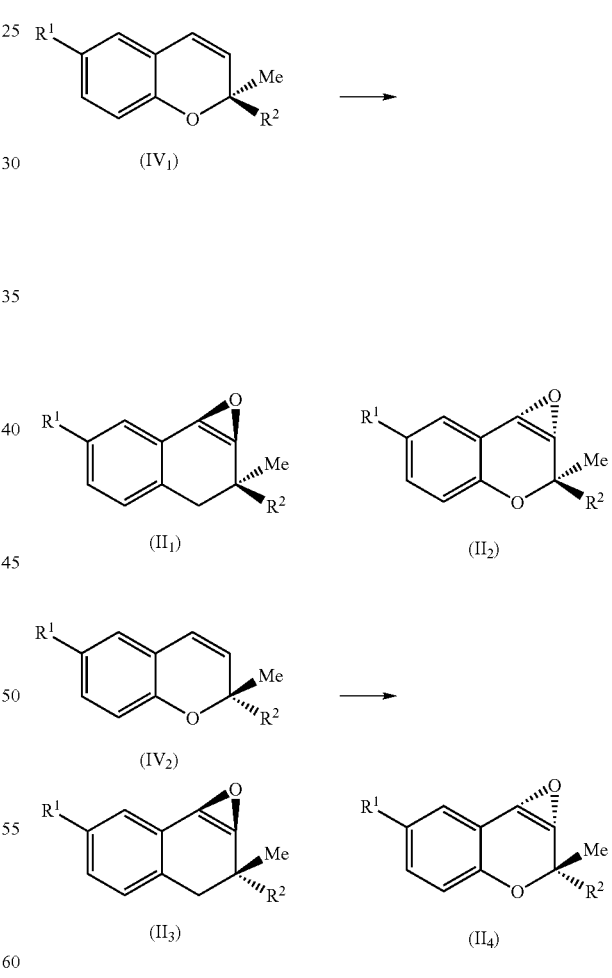

Wherein $R^1$ and $R^2$ are each defined as above formula 1.

(2) Preparation of Secondary Amine Compounds Including Imidazole (III)

Secondary amine compounds including imidazole ring (III), which were used in scheme 1, can be prepared by reductive amination of 2-imidazolecarboxaldehyde and aniline compounds as represented in scheme 3.

Scheme 3

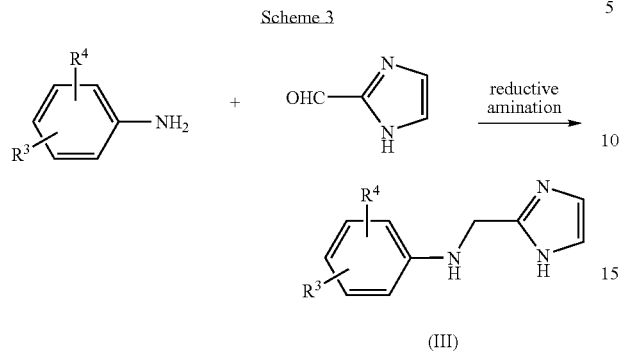

(III)

Wherein $R^3$ and $R^4$ are each defined as above formula 1.

In the above scheme 3, various reducing agents can be employed for reductive amination such as sodium borohydride and sodium cyanoborohydride, etc.

Preferred solvents are alcohols such as methanol, ethanol, etc., or ethyl acetate.

Reaction temperature is preferably maintained from room temperature to the boiling point of solvent employed.

II. Preparation Method

The method for the preparation of compounds (formula 1) comprises the step of reaction of an epoxide compound (II) with secondary amine compound (III) in the presence of proper metal salts.

Metal salts used for this reaction, are $Mg(ClO_4)_2$, $CoCl_2$, $LiClO_4$, $NaClO_4$, $CaCl_2$, $znCl_2$, $LiBF_4$, $Zn(Tf)_2$, etc., and preferable solvents are acetonitrile, tetrahydrofuran, dimethylformamide, etc. Reaction temperature may range from room temperature to boiling point of employed solvent.

In case of using each stereoisomer of the epoxide compound (II) as a starting material, the product with the same configuration to that of the starting material is obtained, respectively. That is, the compounds $(I_1)$, $(I_2)$, $(I_3)$ or $(I_4)$ of formula 1, can be prepared from epoxide compounds $(II_1)$, $(II_2)$, $(II_3)$ or $(II_4)$ with amine compounds (III), respectively.

The compounds (V) of formula 1 whose $R_1$ is $NH_2$ can be prepared by the reduction of the compounds (IV) of which $R^1$ is $NO_2$ as represented in the below scheme 4.

Scheme 4

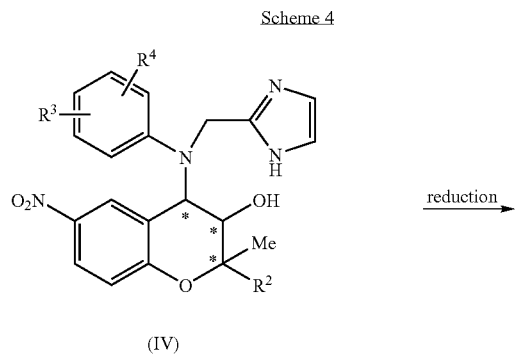

(IV)

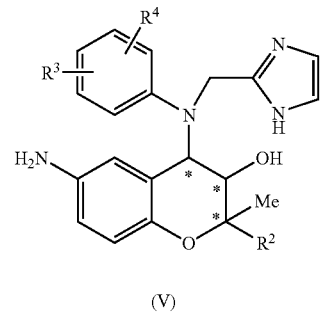

(V)

Wherein $R^2$, $R^3$, $R^4$ and * are each defined as above.

The $NO_2$ group can be reduced to $NH_2$ group by hydrogenation using metal catalysts such as platinum, palladium, palladium on carbon (Pd/C), Raney-nickel, etc. in a suitable solvent. Preferred solvents are alcohols such as methanol, ethanol, etc., and ethyl acetate.

In addition, the reduction of $NO_2$ group to $NH_2$ group can be carried out by using a reducing agent such as $NaBH_4$, etc. in the presence of $CuSO_4$, $Cu(OAc)_2$, $CoCl_2$, $SnCl_2$ or $NiCl_2$, etc. At this time, preferred solvent is a mixture of water and methanol and reaction temperature is from room temperature to boiling point of employed solvent.

In addition, the present invention provides pharmaceutical compositions which contain the benzopyran derivatives substituted with secondary amines including imidazole of the above formula 1 or their pharmaceutically acceptable salts as an active ingredient. In particular, the present invention provides pharmaceutical compositions for suppression of angiogenesis, protection of neuronal cells, brain injury, heart, and organs for preservation or during cardiovascular surgery, and antioxidants.

The compounds of the present invention have an ability to suppress angiogenesis. In detail, the compounds of the present invention inhibit the HUVEC (Human Umbilical Vein Endothelial Cell) tube formation induced by bFGF (basic Fibroblast Growth Factor), and suppress in vivo angiogenesis in mouse matrigel plug assay (subcutaneous and oral administration) and CAM (chorioallantonic membrane assay). Also, the compounds of present invention significantly suppress the tumor growth in nude mouse xenografts of A549 human non small cell lung carcinoma without any significant side effects such as loss of body weights. No mice treated with the compounds of present invention were died, which shows reduced toxicity compared to traditional cytotoxic anti-cancer agents. Therefore, the compounds of present invention can be used for anti-cancer agents and can be applied for the treatment of rheumatoid arthritis and diabetic retinopathies.

In addition, the compounds of the present invention have an ability to protect neurons. In particular, the compounds of the present invention protect neurons from oxidative stress induced by iron and from neuronal cell damage induced by hydrogen peroxide. Therefore, the compounds of the present invention can be used as a neuroprotective and can also be applied for the prevention and treatment of infant asphyxia, glaucoma, diabetic neuropathy, and head trauma caused by neuronal cell damage or death.

Furthermore, the compounds of the present invention inhibit the lipid peroxidation induced by iron or copper, and suppress intracellular reactive oxygen species in A7r5 (Rat thoracic aorta smooth muscle cell line, ATCC) induced by $H_2O_2$. Hence, the compounds of the present invention can be used as an antioxidant and can be effectively applied for the medical treatment of the neurodegenerative disorders caused by lipid peroxydation and the accumulation of free radical species within neurons, such as aging and senile dementia.

In isolated ischemic rat heart model using Langendorff apparatus, the compounds of the present invention significantly prolong the time to contracture (TTC, time to contracture), improve the recovery of postischemic contractile function (LVDP×HR, (left ventricular developing pressure)×(heart rat)), and decrease the release of lactate dehydrogenase (LDH) which is a marker enzyme for cell injury, then show similar cardioprotection effect compared to that of BMS-180448. In addition, the compounds of the present invention have low vasorelaxant activity in contrast to BMS-180448 and BMS-191095. Further, the compounds of the present invention exhibited equal antiischemic activity compared to that of BMS-180448 in the ischemic myocardium injury models of anesthetized rats. As described above, the compounds of the present invention exert excellent anti-ischemic activity both in vitro and in vivo, while show low vasorelaxant activity, so that they can be used as cardioprotectives for the prevention and treatment of myocardial infarction, congestive heart failure, and stable angina.

The present invention includes pharmaceutical formulations used for humans which are prepared in the customary manner by known methods, for example by mixing the active ingredient or ingredients, such as fillers, diluents, binders, humectants, disintegrants, etc.

Solid formulations for Oral administration are tablets, coated tablets, dusting powders, granules, capsules, and pills, which can contain more than one additives in addition to the active ingredient or ingredients, for example starches, calcium carbonate, sucrose, lactose, or gelatin. Besides simple additives, lubricants, for example magnesium stearate and talc, can be used.

Liquid formulations for oral administration are suspension, solution, emulsion, and syrup, which can contain the customary excipients, for example, the liquid diluents such as water and liquid paraffin, wetting agents, sweeteners, preservatives and additives which improve the smell and taste.

Formulations for parenteral administration comprising sterile solutions, suspensions, emulsions, lyophilized powders, and suppositories, etc., can contain, in addition to the active ingredient or ingredients, the customary water-insoluble excipients and suspending agents, for example, propylene glycols, polyethylene glycols, vegetable fats such as olive oil, and injectable esters. Suppositories can contain the customary excipients, for example witepsol, macrogol, tween 61, cacao fat, laurin fat, glycerol, or gelatin, etc.

In general, it has proved advantageous in human medicine to administer the active ingredient or ingredients according to the present invention in total amounts of about 0.01 to about 1000, preferably 0.1 to 500 mg/day based on adults with 70 Kg of body weight, if appropriate in the form of several individual doses, to achieve the desired results. However, it may be necessary to deviate from the dosages mentioned, and in particular to do so as a function of the nature and body weight of the object to be treated, the nature and severity of the disease, the nature of the formulation and of the administration of the medicament and the period or interval within which administration takes place.

Thus in some cases it can suffice to manage with less than the abovementioned amount of active ingredient, while in other cases the abovementioned amount of active ingredient must be exceeded. The particular optimum dosage and mode of administration required for the active ingredient can be determined by any expert on the basis of his expert knowledge.

The molecular structure of the compounds according to the present invention was identified by IR spectroscopy, NMR spectroscopy, mass spectroscopy, liquid chromatography, X-ray diffraction, optical rotation analysis and elemental analysis.

PREPARATION EXAMPLES

Preparation Example

Preparation of Secondary Amines Including Imidazole Heterocycle

4-Chlorophenyl-1H-imidazol-2-ylmethylamine

The solution of 2-imidazolecarboxaldehyde (570 mg, 5.9 mmol) and 4-chloroaniline (756 mg, 5.9 mmol) in methanol (5 ml) was stirred at 60° C. for 4 hours, and allowed to cool to room temperature. To the reaction was added $NaBH_4$ (337 mg, 8.9 mmol), and the mixture was additionally stirred for an hour. Water (20 mL) was added to the reaction, which was extracted with ethyl acetate (50 mL). Organic layer was dried over $MgSO_4$, filtered, and concentrated under reduced pressure. The residue was purified by silica gel column chromatography (5% methanol in chloroform) to give the title compound (660 mg, 53%).

$^1$H NMR (200 MHz, $CDCl_3$) δ 4.27 (s, 3H), 5.40 (brs, 1H), 6.54 (m, 2H), 6.97 (m, 4H).

3-Chlorophenyl-1H-imidazol-2-ylmethylamine $^1$H NMR (200 MHz, $CDCl_3$) δ 4.30 (s, 3H), 6.33-6.47 (m, H), 6.63-6.68 (m, 1H), 6.98 (m, 3H).

4-Methoxyphenyl-1H-imidazol-2-ylmethylamine $^1$H NMR (200 MHz, $CDCl_3$) δ 3.76 (s, 3H), 4.36 (s, 2H), 6.66-6.68 (m, 4H), 6.98 (s, 2H).

2-Methoxyphenyl-1H-imidazol-2-ylmethylamine $^1$H NMR (200 MHz, $CDCl_3$) δ 3.84 (s, 3H), 4.47 (d, 2H, J=4.6 Hz), 4.81 (brs, 1H), 6.52 (dd, 1H, J=8, 1.6 Hz), 6.67-6.86 (m, 3H), 6.98 (s, 2H).

4-Trifluoromethoxyphenyl-1H-imidazol-2-ylmethylamine $^1$H NMR (200 MHz, $CDCl_3$) δ 4.36 (s, 2H), 6.50 (dd, 2H, J=6.8, 2.2 Hz), 6.96-7.26 (m, 4H).

2-Trifluoromethoxyphenyl-1H-imidazol-2-ylmethylamine $^1$H NMR (200 MHz, $CDCl_3$) δ 4.47 (d, 2H, J=5.6 Hz), 4.72 (brs, 1H), 6.61-6.75 (m, 2H), 7.00 (s, 2H), 7.02-7.17 (m, 2H).

4-Trifluoromethylphenyl-1H-imidazol-2-ylmethylamine $^1$H NMR (200 MHz, $CDCl_3$) δ 4.31 (d, 2H, J=5.2 Hz), 6.36 (brs, 1H), 6.68 (d, 2H, J=8.8 Hz), 6.87 (s, 2H), 7.26 (d, 2H, J=8.6 Hz).

2-Trifluoromethylphenyl-1H-imidazol-2-ylmethylamine $^1$H NMR (200 MHz, $CDCl_3$) δ 4.39 (d, 2H, J=5.4 Hz), 5.92 (brs, 1H), 6.68-7.00 (m, 4H), 7.35-7.45 (m, 2H).

4-Methylphenyl-1H-imidazol-2-ylmethylamine $^1$H NMR (200 MHz, $CDCl_3$) δ 2.18 (s, 3H), 4.30 (s, 2H), 6.56 (d, 2H, J=8.4 Hz), 6.88-6.96 (m, 4H).

4-Fluorophenyl-1H-imidazol-2-ylmethylamine $^1$H NMR (200 MHz, $CDCl_3$) δ 4.31 (s, 2H), 6.45-6.61 (m, 2H), 6.71-6.95 (m, 4H).

4-Bromophenyl-1H-imidazol-2-ylmethylamine $^1$H NMR (200 MHz, CDCl$_3$) δ 4.26 (s, 2H), 6.52 (brs, 1H), 6.53-6.58 (m, 2H), 6.87-6.89 (m, 2H), 7.10-7.16 (m, 2H).

2-Isopropylphenyl-1H-imidazol-2-ylmethylamine $^1$H NMR (200 MHz, CDCl$_3$) δ 1.23-1.27 (m, 6H), 4.36 (brs, 1H), 4.47 (s, 2H), 6.54-6.59 (m, 1H), 6.76-6.84 (m, 1H), 6.99-7.28 (m, 4H).

2,6-Dimethylphenyl-1H-imidazol-2-ylmethylamine $^1$H NMR (200 MHz, CDCl$_3$) δ 2.18 (s, 6H), 4.19 (s, 2H), 6.82-6.99 (m, 5H).

2,3-Dimethylphenyl-1H-imidazol-2-ylmethylamine $^1$H NMR (200 MHz, CDCl$_3$) δ 2.07 (s, 3H), 2.24 (s, 3H), 4.38 (s, 2H), 4.56 (brs, 1H), 6.46-6.56 (m, 2H), 6.87-6.95 (m, 3H).

2,4,6-Trimethylphenyl-1H-imidazol-2-ylmethylamine $^1$H NMR (200 MHz, CDCl$_3$) δ 2.16-2.27 (m, 9H), 4.19 (s, 2H), 6.82 (s, 2H), 7.00 (s, 2H).

4-Ethoxycarbonylphenyl-1H-imidazol-2-ylmethylamine $^1$H NMR (200 MHz, CDCl$_3$) δ 1.28 (t, 3H), 4.20 (q, 2H), 4.33 (d, 2H, J=5.2 Hz), 6.54-6.63 (m, 2H), 6.88 (s, 2H), 7.68 (d, 2H, J=8.6 Hz).

1H-imidazol-2-ylmethylbenzylamine $^1$H NMR (200 MHz, CDCl$_3$) δ 3.71-3.83 (m, 4H), 6.90-6.97 (m, 2H), 7.03-7.24 (m, 5H).

Example 1

Preparation of (2S,3S,4R)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran To the solution of the epoxide compound, (2S,3S,4S)-3,4-dihydro-2-dimethoxymethyl-3,4-epoxy-2-methyl-6-nitro-2H-1-benzopyran (437 mg, 1.55 mmol) in acetonitrile (2 mL) was added anhydrous CoCl$_2$ (202 mg, 1.55 mmol). The reaction mixture was stirred at 60° C. for 10 h, then a saturated aqueous solution of NaHCO$_3$ (5 mL) was added to the mixture, which was extracted with ethyl acetate (30 mL). The organic layer was washed with brine, dried over anhydrous Na$_2$SO$_4$, and concentrated under reduced pressure. The residue was purified by silica gel column chromatography (hexane:ethyl acetate=2:1) to yield the title compound (304 mg, 40%).

$^1$H NMR (200 MHz, CDCl$_3$) δ 1.49 (s, 3H), 3.60 (s, 3H), 3.63 (s, 3H), 4.32 (m, 1H), 4.57 (s, 1H), 5.14 (br s, 1H), 6.75 (br s, 2H), 6.97 (m, 4H), 7.27 (m, 2H), 7.93 (s, 1H), 8.08 (d, 1H).

Example 2

Preparation of (2S,3R,4S)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran The title compound (76 mg, 34%) was prepared using (2S,3R,4R)-3,4-dihydro-2-dimethoxymethyl-3,4-epoxy-2-methyl-6-nitro-2H-1-benzopyran (129 mg, 0.46 mmol) and 4-chlorophenyl-1H-imidazol-2-ylmethylamine (95 mg, 0.46 mmol), according to the same procedure used for the preparation of example 1 above.

$^1$H NMR (200 MHz, CDCl$_3$) δ 1.66 (s, 3H), 3.60 (s, 3H), 3.69 (s, 3H), 3.87 (br s, 1H), 4.13 (m, 1H), 4.29 (d, 1H), 4.43 (d, 1H), 4.64 (s, 1H), 5.64 (d, 1H), 6.83 (d, 2H), 6.95 (m, 4H), 7.15 (d, 2H), 7.86 (s, 1H), 8.06 (m, 2H), 8.41 (s, 1H).

Example 3

Preparation of (2R,3R,4S)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran The title compound (76 mg, 34%) was prepared using (2R,3R,4R)-3,4-dihydro-2-dimethoxymethyl-3,4-epoxy-2-methyl-6-nitro-2H-1-benzopyran (129 mg, 0.46 mmol) and 4-chlorophenyl-1H-imidazol-2-ylmethylamine (95 mg, 0.46 mmol), according to the same procedure used for the preparation of example 1 above.

$^1$H NMR (200 MHz, CDCl$_3$) δ 1.49 (s, 3H), 3.60 (s, 3H), 4.32 (m, 1H), 4.57 (s, 1H), 5.14 (br s, 1H), 6.75 (br s, 2H), 6.97 (m, 4H), 7.27 (m, 2H), 7.93 (s, 1H), 8.08 (d, 1H)<

Example 4

Preparation of (2R,3S,4R)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran The title compound (269 mg, 63%) was prepared using (2S,3S,4S)-3,4-dihydro-2-dimethoxymethyl-3,4-epoxy-2-methyl-6-nitro-2H-1-benzopyran (129 mg, 0.46 mmol) and 4-chlorophenyl-1H-imidazol-2-ylmethylamine (183 mg, 0.88 mmol), according to the same procedure used for the preparation of example 1 above.

$^1$H NMR (200 MHz, CDCl$_3$) δ 1.66 (s, 3H), 3.60 (s, 3H), 3.69 (s, 3H), 3.87 (br s, 1H), 4.13 (m, 1H), 4.29 (d, 1H), 4.43 (d, 1H), 4.64 (s, 1H), 5.64 (d, 1H), 6.83 (d, 2H), 6.95 (m, 4H), 7.15 (d, 2H), 7.86 (s, 1H), 8.06 (m, 2H), 8.41 (s, 1H).

Example 5

Preparation of (2S,3S,4R)-3,4-dihydro-2-dimethoxymethyl-3-hydroxy-2-methyl-6-nitro-4-[N-(4-trifluoromethylphenyl)-N-(1H-imidazol-2-ylmethyl)amino]-2H-1-benzopyran The title compound (146 mg, 22%) was prepared using (2S,3S,4S)-3,4-dihydro-2-dimethoxymethyl-3,4-epoxy-2-methyl-6-nitro-2H-1-benzopyran (356 mg, 1.26 mmol) and 4-trifluoromethylphenyl-1H-imidazol-2-ylmethylamine (305 mg, 1.26 mmol), according to the same procedure used for the preparation of example 0.1 above.

$^1$H NMR (200 MHz, CDCl$_3$) δ 1.51 (s, 3H), 3.60 (s, 3H), 3.61 (s, 3H), 4.32 (m, 3H), 4.57 (s, 1H), 5.14 (br s, 1H), 6.85 (m, 2H), 6.95 (m, 4H), 7.38 (d, 2H), 7.91 (s, 1H), 8.05 (dd, 2H), 8.42 (m, 1H).

Example 6

Preparation of (2S,3S,4R)-3,4-dihydro-2-dimethoxymethyl-3-hydroxy-2-methyl-6-nitro-4-[N-(4-methoxyphenyl)-N-(1H-imidazol-2-ylmethyl)amino]-2H-1-benzopyran The title compound (280 mg, 28%) was prepared using (2S,3S,4S)-3,4-dihydro-2-dimethoxymethyl-3,4-epoxy-2- methyl-6-nitro-2H-1-benzopyran (591 mg, 2.10 mmol) and 4-methoxyphenyl-1H-imidazol-2-ylmethylamine (427 mg, 2.10 mmol), according to the same procedure used for the preparation of example 1 above.

$^1$H NMR (200 MHz, CDCl$_3$) δ 1.47 (s, 3H), 3.59 (d, 6H), 3.68 (s, 3H), 4.30 (m, 2H), 4.54 (m, 2H), 5.02 (d, 1H), 6.67-6.78 (m, 4H), 6.89-7.26 (m, 3H), 8.04 (m, 2H).

Example 7

Preparation of (2S,3S,4R)-3,4-dihydro-2-dimethoxymethyl-3-hydroxy-2-methyl-6-nitro-4-[N-(4-trifluoromethoxyphenyl)-N-(1H-imidazol-2-ylmethyl)amino]-2H-1-benzopyran The title compound (181 mg, 47%) was prepared using (2S,3S,4S)-3,4-dihydro-2-dimethoxymethyl-3,4-epoxy-2-methyl-6-nitro-2H-1-benzopyran (200 mg, 0.71 mmol) and 4-trifluoromethoxyphenyl-1H-imidazol-2-ylmethylamine (183 mg, 0.71 mmol), according to the same procedure used for the preparation of example 1 above.

$^1$H NMR (200 MHz, CDCl$_3$) δ 1.50 (s, 3H), 3.60 (d, 6H), 4.2-4.50 (m, 2H), 4.58-5.65 (m, 2H), 5.18 (s, 1H), 6.91-6.95 (m, 7H), 8.00 (s, 1H), 8.05 (dd, 1H).

Example 8

Preparation of (2S,3S,4R)-3,4-dihydro-2-dimethoxymethyl-3-hydroxy-2-methyl-6-nitro-4-[N-(4-bromophenyl)-N-(1H-imidazol-2-ylmethyl)amino]-2H-1-benzopyran The title compound (310 mg, 41%) was prepared using (2S,3S,4S)-3,4-dihydro-2-dimethoxymethyl-3,4-epoxy-2-methyl-6-nitro-2H-1-benzopyran (400 mg, 1.42 mmol) and 4-bromophenyl-1H-imidazol-2-ylmethylamine (359 mg, 1.42 mmol), according to the same procedure used for the preparation of example 1 above.

$^1$H NMR (200 MHz, CDCl$_3$) δ 1.48 (s, 3H), 3.61 (d, 6H), 4.10-4.19 (m, 2H), 4.20-4.40 (m, 2H), 5.13 (s, 1H), 6.70-7.01 (m, 6H), 7.21 (s, 1H), 7.94 (s, 1H), 8.06 (dd, 1H).

Example 9

Preparation of (2S,3S,4R)-3,4-dihydro-2-dimethoxymethyl-3-hydroxy-2-methyl-6-nitro-4-[N-(2,4-dimethylphenyl)-N-(1H-imidazol-2-ylmethyl)amino]-2H-1-benzopyran The title compound (231 mg, 33%) was prepared using (2S,3S,4S)-3,4-dihydro-2-dimethoxymethyl-3,4-epoxy-2-methyl-6-nitro-2H-1-benzopyran (400 mg, 1.42 mmol) and 2,4-dimethylphenyl-1H-imidazol-2-ylmethylamine (287 mg, 1.42 mmol), according to the same procedure used for the preparation of example 1 above.

$^1$H NMR (200 MHz, CDCl$_3$) δ 1.39 (s, 3H), 2.19 (s, 3H), 2.47 (s, 3H), 3.59 (d, 6H), 4.15-4.82 (m, 5H), 6.80-6.89 (m, 5H), 7.58 (d, 1H), 7.94-7.99 (dd, 1H), 8.62 (m, 1H).

Example 10

Preparation of (2S,3S,4R)-3,4-dihydro-2-dimethoxymethyl-3-hydroxy-2-methyl-6-nitro-4-[N-(2-isopropylphenyl)-N-(1H-imidazol-2-ylmethyl)amino]-2H-1-benzopyran The title compound (140 mg, 20%) was prepared using (2S,3S,4S)-3,4-dihydro-2-dimethoxymethyl-3,4-epoxy-2-methyl-6-nitro-2H-1-benzopyran (400 mg, 1.42 mmol) and 2-isopropylphenyl-1H-imidazol-2-ylmethylamine (306 mg, 1.42 mmol), according to the same procedure used for the preparation of example 1 above.

$^1$H NMR (200 MHz, CDCl$_3$) δ 1.22-1.29 (m, 10H), 3.60 (d, 6H), 4.07-4.63 (m, 5H), 6.79-7.35 (m, 6H), 7.78 (m, 1H), 7.99 (dd, 1H), 8.61 (m, 1H).

Example 11

Preparation of (2S,3S,4R)-3,4-dihydro-2-dimethoxymethyl-3-hydroxy-2-methyl-6-nitro-4-[N-(2,3-dimethylphenyl)-N-(1H-imidazol-2-ylmethyl)amino]-2H-1-benzopyran The title compound (253 mg, 37%) was prepared using (2S,3S,4S)-3,4-dihydro-2-dimethoxymethyl-3,4-epoxy-2-methyl-6-nitro-2H-1-benzopyran (400 mg, 1.42 mmol) and 2,3-dimethylphenyl-1H-imidazol-2-ylmethylamine (287 mg, 1.42 mmol), according to the same procedure used for the preparation of example 1 above.

$^1$H NMR (200 MHz, CDCl$_3$) δ 1.39 (s, 3H), 2.17 (s, 3H), 2.41 (s, 3H), 3.61 (d, 6H), 4.26-4.74 (m, 5H), 6.76-6.95 (m, 4H), 6.98 (m, 1H), 7.58 (d, 1H), 7.95 (dd, 1H), 8.63 (d, 1H).

Example 12

Preparation of (2R,3R,4S)-3,4-dihydro-2-dimethoxymethyl-3-hydroxy-2-methyl-6-nitro-4-[N-(2,3-dimethylphenyl)-N-(1H-imidazol-2-ylmethyl)amino]-2H-1-benzopyran The title compound (416 mg, 49%) was prepared using (2R,3R,4R)-3,4-dihydro-2-dimethoxymethyl-3,4-epoxy-2-methyl-6-nitro-2H-1-benzopyran (500 mg, 1.77 mmol) and 2,3-dimethylphenyl-1H-imidazol-2-ylmethylamine (358 mg, 1.77 mmol), according to the same procedure used for the preparation of example 1 above.

$^1$H NMR (200 MHz, CDCl$_3$) δ 1.39 (s, 3H), 2.17 (s, 3H), 2.41 (s, 3H), 3.61 (d, 6H), 4.26-4.74 (m, 5H), 6.76-6.95 (m, 4H), 6.98 (m, 1H), 7.58 (d, 1H), 7.95 (dd, 1H), 8.63 (d, 1H).

Example 13

Preparation of (2R,3R,4S)-3,4-dihydro-2-dimethoxymethyl-3-hydroxy-2-methyl-6-nitro-4-[N-(4-bromophenyl)-N-(1H-imidazol-2-ylmethyl)amino]-2H-1-benzopyran The title compound (570 mg, 60%) was prepared using (2R,3R,4R)-3,4-dihydro-2-dimethoxymethyl-3,4-epoxy-2-methyl-6-nitro-2H-1-benzopyran (500 mg, 1.78 mmol) and 4-bromophenyl-1H-imidazol-2-ylmethylamine (450 mg, 1.78 mmol), according to the same procedure used for the preparation of example 1 above.

$^1$H NMR (200 MHz, CDCl$_3$) δ 1.48 (s, 3H), 3.61 (d, 6H), 4.10-4.19 (m, 2H), 4.20-4.40 (m, 2H), 5.13 (s, 1H), 6.70-7.01 (m, 6H), 7.21 (s, 1H), 7.94 (s, 1H), 8.06 (dd, 1H).

Example 14

Preparation of (2R,3R,4S)-3,4-dihydro-2-dimethoxymethyl-3-hydroxy-2-methyl-6-nitro-4-[N-(4-methoxyphenyl)-N-(1H-imidazol-2-ylmethyl)amino]-2H-1-benzopyran The title compound (446 mg, 86%) was prepared using (2R,3R,4R)-3,4-dihydro-2-dimethoxymethyl-3,4-epoxy-2-methyl-6-nitro-2H-1-benzopyran (300 mg, 1.06 mmol) and 4-methoxyphenyl-1H-imidazol-2-ylmethylamine (216 mg, 1.06 mmol), according to the same procedure used for the preparation of example 1 above.

$^1$H NMR (200 MHz, CDCl$_3$) δ 1.47 (s, 3H), 3.59 (d, 6H), 3.68 (s, 3H), 4.30 (m, 2H), 4.54 (m, 2H), 5.02 (d, 1H), 6.67-6.78 (m, 4H), 6.89-7.26 (m, 3H), 8.04 (m, 2H).

Example 15

Preparation of (2S,3S,4R)-3,4-dihydro-2-dimethoxymethyl-3-hydroxy-2-methyl-6-nitro-4-[N-(4-fluorophenyl)-N-(1H-imidazol-2-ylmethyl)amino]-2H-1-benzopyran The title compound (650 mg, 48%) was prepared using (2S,3S,4S)-3,4-dihydro-2-dimethoxymethyl-3,4-epoxy-2-methyl-6-nitro-2H-1-benzopyran (800 mg, 2.84 mmol) and 4-fluorophenyl-1H-imidazol-2-ylmethylamine (380 mg, 2.0 mmol), according to the same procedure used for the preparation of example 1 above.

$^1$H NMR (200 MHz, CDCl$_3$) δ 1.49 (s, 3H), 3.60 (d, 6H), 4.30 (m, 2H), 4.60 (m, 2H), 5.05 (m, 1H), 6.7$^6$-6.97 (m, 7H), 7.95 (s, 1H), 8.03 (dd, 1H).

Example 16

Preparation of (2S,3S,4R)-3,4-dihydro-2-dimethoxymethyl-3-hydroxy-2-methyl-6-nitro-4-[N-(2-methoxyphenyl)-N-(1H-imidazol-2-ylmethyl)amino]-2H-1-benzopyran The title compound (500 mg, 58%) was prepared using (2S,3S,4S)-3,4-dihydro-2-dimethoxymethyl-3,4-epoxy-2-methyl-6-nitro-2H-1-benzopyran (500 mg, 1.78 mmol) and 2-methoxyphenyl-1H-imidazol-2-ylmethylamine (253 mg, 1.25 mmol), according to the same procedure used for the preparation of example 1 above.

$^1$H NMR (200 MHz, CDCl$_3$) δ 1.38 (s, 3H), 3.60 (d, 6H), 3.91 (s, 3H), 3.97 (m, 1H), 4.74 (d, 1H), 4.60-4.84 (m, 3H), 6.80-7.03 (m, 6H), 7.58 (m, 1H), 7.99 (dd, 1H), 8.86 (m, 1H).

Example 17

Preparation of (2R,3R,4S)-3,4-dihydro-2-dimethoxymethyl-3-hydroxy-2-methyl-6-nitro-4-[N-(2-isopropylphenyl)-N-(1H-imidazol-2-ylmethyl)amino]-2H-1-benzopyran The title compound (72 mg, 42%) was prepared using (2R,3R,4R)-3,4-dihydro-2-dimethoxymethyl-3,4-epoxy-2-methyl-6-nitro-2H-1-benzopyran (100 mg, 0.35 mmol) and 2-isopropylphenyl-1H-imidazol-2-ylmethylamine (75 mg, 0.35 mmol), according to the same procedure used for the preparation of example 1 above.

$^1$H NMR (200 MHz, CDCl$_3$) δ 1.22-1.29 (m, 10H), 3.60 (d, 6H), 4.07-4.63 (m, 5H), 6.79-7.35 (m, 6H), 7.78 (m, 1H), 7.99 (dd, 1H), 8.61 (m, 1H).

Example 18

Preparation of (2R,3R,4S)-3,4-dihydro-2-dimethoxymethyl-3-hydroxy-2-methyl-6-nitro-4-[N-(2-methoxyphenyl)-N-(1H-imidazol-2-ylmethyl)amino]-2H-1-benzopyran The title compound (580 mg, 67%) was prepared using (2R,3R,4R)-3,4-dihydro-2-dimethoxymethyl-3,4-epoxy-2-methyl-6-nitro-2H-1-benzopyran (500 mg, 1.78 mmol) and 2-methoxyphenyl-1H-imidazol-2-ylmethylamine (231 mg, 1.78 mmol), according to the same procedure used for the preparation of example 1 above.

$^1$H NMR (200 MHz, CDCl$_3$) δ 1.38 (s, 3H), 3.60 (d, 6H), 3.91 (s, 3H), 3.97 (m, 1H), 4.74 (d, 1H), 4.60-4.84 (m, 3H), 6.80-7.03 (m, 6H), 7.58 (m, 1H), 7.99 (dd, 1H), 8.86 (m, 1H).

Example 19

Preparation of (2R,3R,4S)-3,4-dihydro-2-dimethoxymethyl-3-hydroxy-2-methyl-6-nitro-4-[N-(3-chlorophenyl)-N-(1H-imidazol-2-ylmethyl)amino]-2H-1-benzopyran The title compound (337 mg, 39%) was prepared using (2R,3R,4R)-3,4-dihydro-2-dimethoxymethyl-3,4-epoxy-2-methyl-6-nitro-2H-1-benzopyran (500 mg, 1.77 mmol) and 3-chloroxyphenyl-1H-imidazol-2-ylmethylamine (366 mg, 1.77 mmol), according to the same procedure used for the preparation of example 1 above.

$^1$H NMR (200 MHz, CDCl$_3$) δ 1.51 (s, 3H), 3.61 (d, 6H), 4.20-4.57 (m, 2H), 4.57-4.59 (m, 2H), 5.17 (s, 1H), 6.69-6.73 (m, 3H), 6.94-7.01 (m, 4H), 7.89 (m, 1H), 8.04 (dd, 1H).

Example 20

Preparation of (2S,3S,4R)-3,4-dihydro-2-dimethoxymethyl-3-hydroxy-2-methyl-6-nitro-4-[N-(3-chlorophenyl)-N-(1H-imidazol-2-ylmethyl)amino]-2H-1-benzopyran The title compound (280 mg, 35%) was prepared using (2S,3S,4S)-3,4-dihydro-2-dimethoxymethyl-3,4-epoxy-2-methyl-6-nitro-2H-1-benzopyran (450 mg, 1.6 mmol) and 3-chloroxyphenyl-1H-imidazol-2-ylmethylamine (232 mg, 1.1 mmol), according to the same procedure used for the preparation of example 1 above.

$^1$H NMR (200 MHz, CDCl$_3$) δ 1.51 (s, 3H), 3.61 (d, 6H), 4.20-4.57 (m, 2H), 4.57-4.59 (m, 2H), 5.17 (s, 1H), 6.69-6.73 (m, 3H), 6.94-7.01 (m, 4H), 7.89 (m, 1H), 8.04 (dd, 1H).

Example 21

Preparation of (2R,3R,4S)-3,4-dihydro-2-dimethoxymethyl-3-hydroxy-2-methyl-6-nitro-4-[N-(4-trifluoromethoxyphenyl)-N-(1H-imidazol-2-ylmethyl)amino]-2H-1-benzopyran The title compound (155 mg, 40%) was prepared using (2R,3R,4R)-3,4-dihydro-2-dimethoxymethyl-3,4-epoxy-2-methyl-6-nitro-2H-1-benzopyran (200 mg, 0.71 mmol) and 4-trifluoromethoxyphenyl-1H-imidazol-2-ylmethylamine (183 mg, 0.71 mmol), according to the same procedure used for the preparation of example 1 above.

¹H NMR (200 MHz, CDCl₃) δ 1.49 (s, 3H), 3.60 (d, 6H), 4.20-4.50 (m, 2H), 4.58-5.65 (m, 2H), 5.18 (s, 1H), 6.91-6.95 (m, 7H), 7.99 (s, 1H), 8.04 (dd, 1H).

Example 22

Preparation of (2S,3S,4R)-6-cyano-3,4-dihydro-2-dimethoxymethyl-3-hydroxy-2-methyl-4-[N-(4-chlorophenyl)-N-(1H-imidazol-2-ylmethyl)amino]-2H-1-benzopyran The title compound (106 mg, 28%) was prepared using (2S,3S,4S)-6-cyano-3,4-dihydro-2-dimethoxymethyl-3,4-epoxy-2-methyl-2H-1-benzopyran (210 mg, 0.8 mmol) and 4-chlorophenyl-1H-imidazol-2-ylmethylamine (167 mg, 0.8 mmol), according to the same procedure used for the preparation of example 1 above.

¹H NMR (200 MHz, CDCl₃) δ 1.47 (s, 3H), 3.58 (s, 3H), 3.62 (s, 3H), 4.35 (m, 1H), 4.57 (s, 1H), 5.16 (br s, 1H), 6.81-6.93 (m, 3H), 7.17 (d, 1H), 7.38 (s, 1H), 7.51 (dd, 1H).

Example 23

Preparation of (2R,3R,4S)-6-amino-3,4-dihydro-2-dimethoxymethyl-3-hydroxy-2-methyl-4-[N-(4-chlorophenyl)-N-(1H-imidazol-2-ylmethyl)amino]-2H-1-benzopyran To the solution of the nitro compound (521 mg, 1.07 mmol) prepared from example 3 in methanol (3 mL) was added 10% Pd/C. The mixture was hydrogenated at room temperature under 3 atmosphere pressure of H₂ for 12 hours, and filtered through a pad of Celite. The filtrate was concentrated, and the residue was purified by silica gel column chromatography (5% methanol in dichloromethane) to afford the title compound (368 mg, 75%).

¹H NMR (200 MHz, CDCl₃) δ 1.42 (s, 3H), 3.61 (s, 6H), 4.27 (m, 2H), 4.42 (s, 1H), 4.52 (d, 1H), 5.24 (m, 1H), 6.29 (s, 1H), 6.58 (d, 2H), 6.70 (d, 2H), 6.98 (m, 3H), 7.41 (m, 2H).

Example 24

Preparation of (2S,3S,4R)-6-amino-3,4-dihydro-2-dimethoxymethyl-3-hydroxy-2-methyl-4-[N-(4-chlorophenyl)-N-(1H-imidazol-2-ylmethyl)amino]-2H-1-benzopyran To the solution of the nitro compound (177 mg, 0.36 mmol) prepared from example 1 in methanol (2 mL) was added a 0.4 M aqueous solution of Cu(OAc)₂ (0.38 mL, 0.15 mmol), then slowly added sodium borohydride (113 mg, 3.0 mmol) over 30 min. The reaction mixture was stirred for an hour at room temperature, and ethyl acetate (5 mL) was added to the reaction. The black precipitates were removed by filtration, then to the filtrate was added a saturated aqueous solution of NaHCO₃ (5 mL). The mixture was extracted with ethyl acetate (30 mL), and the organic layer was washed with brine, dried over Na₂SO₄, filtered, and concentrated under reduced pressure. The residue was purified by silica gel column chromatography (n-hexane:ethyl acetate=1:4) to afford the title compound (58 mg, 35%).

¹H NMR (200 MHz, CDCl₃) δ 1.42 (s, 3H), 3.61 (s, 6H), 4.27 (m, 2H), 4.52 (d, 1H), 4.42 (s, 1H), 5.24 (m, 1H), 6.29 (s, 1H), 6.58 (d, 2H), 6.70 (d, 2H), 6.98 (m, 3H), 7.41 (m, 2H).

Example 25

Preparation of (2S,3S,4R)-6-amino-3,4-dihydro-2-dimethoxymethyl-3-hydroxy-2-methyl-4-[N-(4-trifluoromethylphenyl)-N-(1H-imidazol-2-ylmethyl)amino]-2H-1-benzopyran The title compound (34 mg, 57%) was prepared using the nitro compound (65 mg, 0.12 mmol) obtained from example 5, according to the same procedure used for the preparation of example 24 above.

¹H NMR (200 MHz, CDCl₃) δ 1.38 (s, 3H), 3.60 (s, 3H), 4.06-4.85 (m, 3H), 4.41 (s, 1H), 5.06 (br s, 2H), 6.31 (s, 1H), 6.57 (d, 2H), 6.80-7.18 (m, 7H).

Example 26

Preparation of (2R,3R,4S)-6-amino-3,4-dihydro-2-dimethoxymethyl-3-hydroxy-2-methyl-4-[N-(4-trifluoromethoxyphenyl)-N-(1H-imidazol-2-ylmethyl)amino]-2H-1-benzopyran The title compound (23 mg, 24%) was prepared using the nitro compound (100 mg, 0.19 mmol) obtained from example 21, according to the same procedure used for the preparation of example 23 above.

¹H NMR (200 MHz, CDCl₃) δ 1.50 (s, 3H), 3.60 (d, 6H), 4.20-4.50 (m, 2H), 4.59 (s, 2H), 5.18 (s, 1H), 6.30 (s, 1H), 6.60 (dd, 2H), 6.70-6.96 (m, 6H).

Example 27

Preparation of (2R,3R,4S)-6-amino-3,4-dihydro-2-dimethoxymethyl-3-hydroxy-2-methyl-4-[N-(2,3-dimethylphenyl)-N-(1H-imidazol-2-ylmethyl)amino]-2H-1-benzopyran The title compound (19 mg, 15%) was prepared using the nitro compound (135 mg, 0.28 mmol) obtained from example 12, according to the same procedure used for the preparation of example 23 above.

¹H NMR (200 MHz, CDCl₃) δ 1.29 (s, 3H), 2.27 (s, 3H), 2.43 (s, 3H), 3.60 (s, 6H), 4.41-4.63 (m, 5H), 6.57 (dd, 1H), 6.70-7.19 (m, 6H), 7.40 (d, 1H).

Example 28

Preparation of (2R,3R,4S)-6-amino-3,4-dihydro-2-dimethoxymethyl-3-hydroxy-2-methyl-4-[N-(4-methoxyphenyl)-N-(1H-imidazol-2-ylmethyl)amino]-2H-1-benzopyran The title compound (21 mg, 23%) was prepared using the nitro compound (100 mg, 0.21 mmol) obtained from example 14, according to the same procedure used for the preparation of example 23 above.

¹H NMR (200 MHz, CDCl₃) δ 1.36 (s, 3H), 3.60 (d, 6H), 3.64 (s, 3H), 4.20-4.60 (m, 3H), 4.45 (s, 1H), 4.70-4.90 (m, 2H), 6.50 (m, 1H), 6.70 (dd, 1H), 6.80-7.00 (m, 6H), 7.40 (d, 1H).

Example 29

Preparation of (2R,3R,4S)-6-amino-3,4-dihydro-2-dimethoxymethyl-3-hydroxy-2-methyl-4-[N-(4-bromophenyl)-N-(1H-imidazol-2-ylmethyl)amino]-2H-1-benzopyran The title compound (50 mg, 53%) was prepared using the nitro compound (100 mg, 0.19 mmol) obtained from example 13, according to the same procedure used for the preparation of example 23 above.

$^1$H NMR (200 MHz, CDCl$_3$) δ 1.48 (s, 3H), 3.61 (d, 6H), 4.10-4.19 (m, 2H), 4.22 (s, 2H), 5.13 (s, 1H), 6.33-7.15 (m, 9H).

Example 30

Preparation of (2S,3S,4R)-6-amino-3,4-dihydro-2-dimethoxymethyl-3-hydroxy-2-methyl-4-[N-(2,3-dimethylphenyl)-N-(1H-imidazol-2-ylmethyl)amino]-2H-1-benzopyran The title compound (35 mg, 54%) was prepared using the nitro compound (70 mg, 0.14 mmol) obtained from example 11, according to the same procedure used for the preparation of example 23 above.

$^1$H NMR (200 MHz, CDCl$_3$) δ 1.29 (s, 3H), 2.27 (s, 3H), 2.43 (s, 3H), 3.60 (s, 6H), 4.41-4.63 (m, 5H), 6.57 (dd, 1H), 6.70-7.19 (m, 6H), 7.40 (d, 1H).

Example 31

Preparation of (2S,3S,4R)-6-amino-3,4-dihydro-2-dimethoxymethyl-3-hydroxy-2-methyl-4-[N-(2-methoxyphenyl)-N-(1H-imidazol-2-ylmethyl)amino]-2H-1-benzopyran The title compound (74 mg, 66%) was prepared using the nitro compound (80 mg, 0.16 mmol) obtained from example 16, according to the same procedure used for the preparation of example 23 above.

$^1$H NMR (200 MHz, CDCl$_3$) δ 1.30 (s, 3H), 3.60 (d, 6H), 3.80 (s, 3H), 4.10-4.30 (m, 2H), 4.45 (s, 1H), 4.70-4.90 (m, 2H), 6.50 (dd, 1H), 6.70-7.00 (m, 7H), 7.40 (d, 1H).

Example 32

Preparation of (2S,3S,4R)-6-amino-3,4-dihydro-2-dimethoxymethyl-3-hydroxy-2-methyl-4-[N-(4-methoxyphenyl)-N-(1H-imidazol-2-ylmethyl)amino]-2H-1-benzopyran The title compound (74 mg, 77%) was prepared using the nitro compound (103 mg, 0.21 mmol) obtained from example 6, according to the same procedure used for the preparation of example 23 above.

$^1$H NMR (200 MHz, CDCl$_3$) δ 1.36 (s, 3H), 3.60 (d, 6H), 3.64 (s, 3H), 4.20-4.60 (m, 3H), 4.45 (s, 1H), 4.70-4.90 (m, 2H), 6.50 (m, 1H), 6.70 (dd, 1H), 6.80-7.00 (m, 6H), 7.40 (d, 1H).

Example 33

Preparation of (2S,3S,4R)-6-amino-3,4-dihydro-2-dimethoxymethyl-3-hydroxy-2-methyl-4-[N-(2,4-dimethylphenyl)-N-(1H-imidazol-2-ylmethyl)amino]-2H-1-benzopyran The title compound (54 mg, 67%) was prepared using the nitro compound (86 mg, 0.18 mmol) obtained from example 9, according to the same procedure used for the preparation of example 23 above.

$^1$H NMR (200 MHz, CDCl$_3$) δ 1.26 (s, 3H), 2.20 (s, 3H), 2.43 (s, 3H), 3.58 (s, 6H), 4.36-4.54 (m, 3H), 4.60 (m, 2H), 6.56 (dd, 1H), 6.70 (dd, 1H), 6.80-7.15 (m, 6H), 7.36 (d, 1H).

Example 34

Preparation of (2S,3S,4R)-6-amino-3,4-dihydro-2-dimethoxymethyl-3-hydroxy-2-methyl-4-[N-(2-isopropylphenyl)-N-(1H-imidazol-2-ylmethyl)amino]-2H-1-benzopyran The title compound (30 mg, 73%) was prepared using the nitro compound (45 mg, 0.09 mmol) obtained from example 10, according to the same procedure used for the preparation of example 23 above.

$^1$H NMR (200 MHz, CDCl$_3$) δ 1.22-1.29 (m, 9H), 3.60 (d, 6H), 4.10-4.62 (m, 5H), 6.50-6.77 (m, 2H), 6.85-7.30 (m, 6H), 7.60 (m, 1H).

Example 35

Preparation of (2S,3S,4R)-6-amino-3,4-dihydro-2-dimethoxymethyl-3-hydroxy-2-methyl-4-[N-(4-trifluoromethoxyphenyl)-N-(1H-imidazol-2-ylmethyl)amino]-2H-1-benzopyran The title compound (34 mg, 72%) was prepared using the nitro compound (50 mg, 0.10 mmol) obtained from example 7, according to the same procedure used for the preparation of example 23 above.

$^1$H NMR (200 MHz, CDCl$_3$) δ 1.50 (s, 3H), 3.60 (d, 6H), 4.20-4.50 (m, 2H), 4.59 (s, 2H), 5.18 (s, 1H), 6.30 (s, 1H), 6.60 (dd, 2H), 6.70-6.96 (m, 6H).

Example 36

Preparation of (2S,3S,4R)-6-amino-3,4-dihydro-2-dimethoxymethyl-3-hydroxy-2-methyl-4-[N-(4-bromophenyl)-N-(1H-imidazol-2-ylmethyl)amino]-2H-1-benzopyran The title compound (41 mg, 88%) was prepared using the nitro compound (50 mg, 0.10 mmol) obtained from example 8, according to the same procedure used for the preparation of example 23 above.

$^1$H NMR (200 MHz, CDCl$_3$) δ 1.48 (s, 3H), 3.61 (d, 6H), 4.10-4.19 (m, 2H), 4.22 (s, 2H), 5.13 (s, 1H), 6.33-7.15 (m, 9H).

Example 37

Preparation of (2S,3S,4R)-6-amino-3,4-dihydro-2-dimethoxymethyl-3-hydroxy-2-methyl-4-[(N-(4-fluorophenyl)-N-(1H-imidazol-2-ylmethyl)amino]-2H-1-benzopyran The title compound (44 mg, 95%) was prepared using the nitro compound (50 mg, 0.10 mmol) obtained from example 15, according to the same procedure used for the preparation of example 23 above.

$^1$H NMR (200 MHz, CDCl$_3$) δ 1.49 (s, 3H), 3.60 (d, 6H), 4.30 (m, 4H), 4.98 (s, 1H), 6.33 (s, 1H), 6.55 (dd, 2H), 6.60-6.92 (m, 6H).

EXPERIMENTAL EXAMPLES

The following experiments were made on the compounds of the formula 1 to investigate their pharmacological actions.

Experimental Example 1

Inhibitory Effects on HUVEC Tube Formation

The Inhibitory effects of the compounds of the formula 1 on angiogenesis were meassured by the vascular tube formation assay of HUVECs (Human umbilical vein endothelial cells), which is one of the major angiogenic steps.

HUVECs were isolated from human umbilical vein, and cultured. HUVECs within passage 5 from confluent cultures were detached, and plated onto a layer of a bFGF (basic fibroblast growth factor)-reduced and polymerized Matrigel. Matrigel cultures were incubated with or without the compounds of formula 1, and the changes of cell morphology were captured through a phase contrast microscope and photographed.

The effects on tube formation of the test compounds were compared with the vehicle treated controls, then confirmed their in vitro anti-angiogenic effect indirectly. The results are given in table 1.

TABLE 1

Inhibitory Effects on HUVEC Tube Formation

| Example | Tube formation | | |
|---------|------|------|------|
|         | 10 μM | 50 μM | 100 μM |
| Example 1 | + | + | ++ |
| Example 2 | ++ |   | +++ |
| Example 3 |   | ++ |   |
| Example 4 |   | + |   |
| Example 5 |   | ++ |   |
| Example 6 |   | + |   |
| Example 7 |   | + |   |
| Example 8 |   | + |   |
| Example 9 |   | + |   |
| Example 10 |   | ++ |   |
| Example 12 |   | + |   |
| Example 13 |   | + |   |
| Example 14 |   | + |   |
| Example 22 | + |   | ++ |
| Example 23 |   | +++ |   |
| Example 24 | + |   | + |
| Example 25 | +/− |   | +/− |
| Example 26 |   | + |   |
| Example 27 |   | +/− |   |

TABLE 1-continued

Inhibitory Effects on HUVEC Tube Formation

| Example | Tube formation | | |
|---------|------|------|------|
|         | 10 μM | 50 μM | 100 μM |
| Example 28 |   | + |   |
| Example 29 |   | + |   |

−; no inhibition,
+/−; week inhibition,
+; moderate inhibition,
++; strong inhibition
+++; complete inhibition As seen in table 1, the compound of example 2 showed potent inhibitory effects on HUVEC tube formation in a dose-dependent manner with strong inhibition at 10 uM, and complete inhibition at 100 uM. The compounds of example 3, 5, and 10 strongly inhibited HUVEC tube formation at 50 uM, and in particular, the compound of example 23 didn't show any tube like structures at 50 uM. The compounds of the present invention demonstrated antiangiogenic actions by inhibiting vascular tube formation, one of major angiogenic steps.

With such an excellent suppressive activity against angiogenesis, the compounds of the present invention can be usefully applied for the treatment of various diseases induced by angiogenesis, such as cancers, rheumatoid arthritis, diabetic retinopathy, psoriasis, and AIDS complications, etc.

Experimental Example 2

In Vivo Mouse Matrigel Plug Assay

Antiangiogenic activities in vivo of the compounds of the formula 1 were determined by mouse matrigel plug assay.

The mixture of Matrigel, heparin (30 units), and bFGF (25 ng) were injected subcutaneously into C57BL/6 mice. The test compounds were injected subcutaneously at 2.2 mg/mL with matrigel, or administrated orally at 2 mg/day (twice a day, each 1 mg) during 4 days (total 8 mg/mouse). After 4-7 days, the skin of the mouse was pulled back, and matrigel plug was excised. The hemoglobin contents inside the Matrigel plugs were measured using the Drabkin method and Drabkin reagent (kit 525, Sigma) for the quantitation of blood vessel formation. The results are given in table 2.

TABLE 2

| In vivo mouse matrigel plug assay | | |
|---|---|---|
|  | % Inhibition | |
|  | S. C | oral |
| control | 0 | 0 |
| Example 1 | 79 | 94 |

As shown in table 2, the compound of example 1 markedly inhibited the hemoglobin quantity to 79%, or 94% each, by subcutaneous injection (2.2 mg/mL) or oral administration (8.8 mg/mouse), which demonstrated the antiangiogenic activity in vivo.

With such an excellent suppressive in vivo activity against angiogenesis, the compounds of the present invention can be usefully applied for the treatment of various diseases induced by angiogenesis, such as cancers, rheumatoid arthritis, diabetic retinopathy, psoriasis, and AIDS complications, etc.

Experimental Example 3

CAM (Chorioallatonic Membrane) Assay

Chick chorioallantoic membrane (CAM) assays were performed to measure the inhibitory effects on angiogenesis in vivo of the compounds of the formula 1.

Fertilized chick eggs were incubated under constant humidified (90%) egg breeder at 37° C. On the third day of incubation, about 2 mL of egg albumin was aspirated by an 18-gauge hypodermic needle through the small hole drilled at the narrow end of the eggs, to detach the developing CAM from the shell. And the shell covering the air sac was punched out and removed by forcep, and the shell membrane on the floor of the air sac was peeled away. After more incubation of two more days, sample-loaded thermanox coverslips were air-dried, and applied to the CAM surface to test the angiogenic inhibition by the test compounds. Three days later, 1 to 2 mL of 10% fat emulsion (Intralipose) was injected into the chorioallantoic and observed avascular zone under a dissecting microscope. The negative control was implanted only thermanox coverslip, while the positive control was treated with retinoic acid (1 μg/egg). The response that CAM showed similar avascular zone to that treated with retinoic acid was scored as positive, and the percentage of positive eggs to total numbers of eggs tested was calculated (%). Independent experiment was repeated three times and at least more than 20 eggs in each experiment were used.

TABLE 3

Anti-angiogenic activity in CAM assay

| | % Inhibition | |
|---|---|---|
| | 0.5 μM/egg | 1.5 μg/egg |
| Example 1 | 62 | 84 |

The negative control implanted only thermanox coverslip formed new branches from the existing vessels, demonstrating normal vascular development similar to that observed with untreated CAM. The positive control treated with retinoic acid significantly inhibited microvessel formation, especially larger vessels formation. The compound of example 1 showed 62% and 84% inhibition at the concentration of 0.5 μg/egg, and 1.5 μg/egg, each. The positive responses by the compound of example 1 was significant, and the inhibitory effect on chicken embryonic angiogenesis was dose-dependent.

With such an excellent anti-angiogenic activities on in vivo CAM assay, the compounds of the present invention can be usefully applied for the treatment of various diseases induced by angiogenesis, such as cancers, rheumatoid arthritis, diabetic retinopathy, psoriasis, and AIDS complications, etc.

Experimental Example 4

Human Tumor Xenografts in Nude Mice

Human tumor xenograft experiments were performed to evaluate whether the compounds of the formula 1 inhibit growth of human tumors implanted in nude mice.

Nude mice (BALB/c nu/nu, male) were purchased from Charls River Japan, Inc., and housed and treated under SPF (Special Pathogen Free) facilities according to the regulation of NIH (national institutes of health). A549 cells isolated from human non small cell lung cancer (NSCLC) were purchased from ATCC (American tissue cancer collection, USA), and maintained as an exponentially growing monolayer in Korea Research Institute of Chemical Technology. Effects of the compounds of present invention on implanted tumor growth were measured by the comparison of tumor sizes, in addition, the changes of body weights and survival % of nude mice were observed.

(1) Inhibition on A549 NSCLC Growth

Nude mice had been adjusted to the laboratory for 2-3 weeks after purchase, and all procedures were performed on male mice of 8 weeks of age, within a weight range of 18-20 g.

A549 tumor xenografts were established in the right flank of mice by subcutaneous injection of cells in 3×3×3 $mm^3$ size of culture. 24 hours after cell implantation, the administration of the compounds was started and which day is defined as day 1. Nude mice were injected intraperitoneally with the compound of example 23 (50 mg/kg) or vehicle (PBS containing 0.5% tween 80) once daily from day 1 to day 20. Tumor volume (V) was assessed by caliper measurement using the mathematical formula 1, where a was the longest diameter across the tumor and b was the corresponding perpendicular short diameter.

$$Volume\ (mm^3)=a\times b^2/2 \qquad \text{[Mathematical Formula 1]}$$

Inhibition (%) was calculated as $(1-(V_T)_n/-(V_C)_n)\times 100$, where $(V_T)_n$ and $(V_C)_n$ were the mean tumor volume of treated and control group at n days after administration of the compound. Each group consisted of 8 mice, and statistical significance was represented as student-T test (* p<0.05).

TABLE 4

Inhibition of the compounds on A549 NSCLC growth in nude mice xenografts

| | Tumor volume ($mm^3$), Inhibition (%) | | | |
|---|---|---|---|---|
| | 25 days | 35 days | 45 days | 65 days |
| Control | 152.9 | 308.5 | 483.9 | 1034.9 |
| Example 23 (50 mg/Kg) (Inhibition %) | 92.2 (40%) | 186.8 (39%) | 244.3* (50%) | 494.8* (52%) |

As represented in table 4, the compound of example 23 significantly inhibited A549 NSCLC growth from 45 days to 61 days after implantation by 50-52%. With such an excellent anti-cancer activity in vivo human tumor xenografts experiment as well as anti-angiogenic properties, the compounds of the present invention can be usefully applied as anti-cancer agents.

(2) Effects on Changes of Body Weights

The effects of the compounds of the formula 1 on changes of body weights were determined. Body weights of nude mice were measured using AND balance at 5 day intervals starting from the date of administration of compounds, and represented as a mean value of treated group ($W_C$) and control group ($W_T$), respectively.

TABLE 5

Effects of the compounds of formula 1 on changes of body weight in nude mice implanted A549

| | Body weight (g) | | | |
|---|---|---|---|---|
| | 1 day | 14 days | 25 days | 35 days |
| Control | 22.50 | 25.16 | 25.43 | 25.88 |
| Example 23 (50 mg/Kg) | 22.30 | 25.42 | 26.17 | 27.10 |

As shown in table 5, retardation or loss of body weight gain was not observed by the treatment of the compound of example 23, then the compounds of present invention cab be used as anti-cancer agents without side effects of retardation or loss of weight gain.

(3) Effects on Survival Percents of Mice

Survival percents of mice were measured to determine the toxicity by administration of the compounds of the formula 1, and to demonstrate the survival rate of A549 implanted mice as time passed. Survival percents were represented using following mathematical formula 2, where $N_0$ is the number of mice at the first day of administration, and $N_n$ is the number of mice at n days after administration.

Survival %=$N_n/N_0$×100      [Mathematical formula 2]

TABLE 6

Effects on survival % of the compounds in A549 implanted mice

| | Survival % | | | |
|---|---|---|---|---|
| | 1 day | 5 days | 15 days | 20 days |
| Control | 100% | 100% | 100% | 100% |
| Example 23 (50 mg/Kg) | 100% | 100% | 100% | 100% |

As seen in table 6, the compound of example 23 showed 100% of survival rate, which demonstrates the significantly reduced side effects and toxicities compared to the traditional cytotoxic anti-cancer agents. As described above the compounds of present invention show the excellent inhibition on tumor growth with significantly reduced toxicities, therefore the compounds of present invention can be usefully applied as anti-cancer agents.

Experimental Example 5

Protective Activities Against Iron-Induced Neuronal Damage

In order to examine whether the compounds of the formula 1 suppress the iron-induced neuronal damage and death, experiments were conducted as follows.

From the brains of 17-18 day-old rat embryos, cerebral cortical neurons were isolated and then, cultured at 37° C. for 7-9 days in a 5% $CO_2$ incubator. The cortical cell cultures were washed twice with a minimum essential medium (MEM) to reduce the serum concentration to 0.2% and pre-treated with test compounds at 30, 7.5, 1.875, and 0.469 μM of final concentrations, each for 30 min. The test compounds were dissolved in DMSO and diluted in a medium. At this time, the final concentration of DMSO was not allowed to exceed 0.2%. For a control group, only vehicle was applied.

After the pre-treatment with test compounds or vehicle, $FeSO_4$ was added to a final concentration of 50 μM, and the cultures were maintained for 24 hours in a $CO_2$ incubator. During incubation, lactate dehydrogenase (LDH) was released into the medium upon neuronal death by the oxidative toxicity of iron. The extent of neuronal damage was assessed by measuring the amount of LDH released into the media. The protective effect of the compounds of interest on neurons was evaluated by calculating the reduction rate of released LDH of treated group compared with that of the control group, and $IC_{50}$ was calculated as the least linear regression analysis of dose-response curve. The results are given in Table 7, below.

TABLE 7

Protective Effect of Compounds of Formula 1 on Neurons

| | Neuroprotection | |
|---|---|---|
| Compound | inhibition % (30 μM) | $IC_{50}$ (μM) |
| Example 2 | 92% | 6.2 |

As seen in Table 7, the compound of example 2 showed 92% of inhibition on LDH release with the $IC_{50}$ of 6.2 μM, which demonstrates that the compound has very potent protective activity against the iron-included damage to neurons.

Since the compounds of the present invention showed an excellent protective effects on neurons, they can be used as preventive or curative agents for the medical treatment of the neurological disorders caused by the damage or death of neurons, such as cerebral stroke and dementia as well as for the medical treatment of inflammatory diseases such as arthritis, cardiac infarction, and acute/chronic tissue damage.

Experimental Example 6

Inhibitory Activity Against Iron-induced Lipid Peroxidation

In order to examine whether the compounds of the formula 1 suppress the iron-induced lipid peroxidation, experiments were conducted as follows.

The rat brain was homogenized in a Krebs buffer (15 mM HEPES, 10 mM glucose, 140 mM NaCl, 3.6 mM KCl, 1.5 mM $CaCl_2$, 1.4 mM $KH_2PO_4$, 0.7 mM $MgCl_2$, pH 7.4) and the supernatant separated by centrifugation at 12,000 rpm for 10 min was used for further experiments. $FeCl_2$ was added to a final concentration of 400 μm in the brain homogenate which was then allowed to stand at 37° C. for 30 min. for the facilitation of oxidation. Each of the test compounds was added at a concentration of 30 μM and vehicle was used as a control.

Iron facilitates the oxidation of the brain homogenate to produce malondialdehyde (MDA), a lipid peroxidation product. Thus, the lipid peroxidation was determined by MDA quantification. The inhibitory effect of the test compounds against the lipid peroxidation was evaluated by calculating MDA reduction rate of the test compounds compared with that of the control group.

Typically, the MDA quantification is achieved by reacting samples with 2-thiobarbituric acid (TBA) and measuring the absorbance at 530 nm. However, this method is unsuitable to treat samples on a large scale because of a boiling step.

Thus, in this experiment, N-methyl-2-phenylindole was used instead of TBA. In this case, one molecule of MDA reacts with two molecules of N-methyl-2-phenylindole to form a chromogen which shows a maximal absorbance at 586 nm and requires no boiling steps. Bioxytech$^R$ LPO-586 Kit was used for MDA quantification. The results are given in Table 8, below.

TABLE 8

Inhibitory Effect of Compounds of Formula 1 on Lipid Peroxidation by iron

| Compounds | Concentration (μM) | % Inhibition |
|---|---|---|
| Example 24 | 30 | 83 |
| Example 25 | 30 | 97 |

As seen in Table 8, the compounds of the present invention suppress the iron-induced lipid peroxidation. In particular, the compounds of Examples 24 and 25 showed very potent inhibitory activity against the iron-induced lipid peroxidation with inhibitory effects of 83% and 97%, respectively at the concentration of 30 μM.

With excellent inhibitory activity against lipid peroxidation, the compounds of the present invention can be used for the prevention and treatment of neurodegenerative diseases such as cerebral stroke and dementia, inflammatory diseases such as arthritis, cardiac infarction, and acute/chronic tissue damage, which may be caused by the lipid peroxidation and its accumulation in tissues.

Experimental Example 7

Vasorelaxation Effects on Isolated Blood Vessels of Rats

The following experiment was conducted to examine whether the compounds of the formula 1 have vasorelaxation effects.

Male Sprague-Dawly rats (350-450 g, obtained from the Experimental Animal Team of the Korea Research Institute of Chemical Technology) were knocked unconscious by hitting the occipital region, sacrificed by cervical dislocation, and underwent thoracotomy. After being quickly removed, the thoracic aorta was deprived of the adipose tissue and cut into aortic rings of 3 mm width. The aorta was lightly rubbed with a modified Krebs Henseleit buffer (Physiological Salt Solution, PSS) soaked cotton club to remove the inner epithelial layer therefrom. While being suspended in an organ bath containing a physiological buffer, the vascular tissue was allowed to equilibrate under a resting tension of 2 g and then, stand for 1 hour at 37° C. for stabilization with a supply of a carbogen consisting of 95% $O_2$-5% $CO_2$.

Thereafter, the vascular tissue was constricted with $10^{-5}$ M phenylephrine and washed several times with PSS and this procedure was repeated again to ensure the stable reactivity of vascular smooth muscle to repetitive constriction/dilatation.

In addition, $3\times10^{-6}$ M methoxamine was used to induce an intensive constriction in the vascular smooth muscle. When the vasoconstriction induced by the methoxamine reached and maintained a maximum, test compounds and controls were cumulatively added to the organ baths in concentrations of 1, 3, 10 and 30 μM so as to induce vasodilatation. Cromakalim, BMS-180448, and BMS-191095 were used as the controls.

Following the addition of test compounds, the change in the maximal constriction induced by methoxamine was calculated to plot a concentration-relaxation response curve. Through a linear regression analysis, $IC_{50}$, the drug concentration at which the vascular tissue is 50% dilated, was obtained for each compound. The results are given in Table 9, below.

TABLE 9

Vasorelaxation effects of the Compounds of formula 1 on Methoxamine Induced Vasoconstriction

| Compounds | Vasorelaxation Effects ($IC_{50}$, μM) |
|---|---|
| Cromakalim | 0.067 |
| BMS-180448 | 1.38 |
| BMS-191095 | 2.14 |
| Example 1 | 9.83 |

Cromakalim showed a potent vasorelaxation effect with 0.067 μM of $IC_{50}$ on the isolated rat aorta constricted with methoxamine (3 μM), while $IC_{50}$ of BMS-180448 and BMS-191095 were 1.38, and 2.14 μM respectively, showing vasodrelaxation potencies twenty times and thirty times as weak as Cromakalim. On the other hand, the compound of example 1 represented 9.83 μM of $IC_{50}$, so that its vasorelaxation effect was significantly weaker than the controls, Cromakalim, BMS-180448, and BMS-191095.

When exerting their actions on the KATP present in the heart, the compounds according to the present invention play a role in protecting the heart. On the other hand, the KATP openers acting on the KATP present in peripheral vascular smooth muscle dilate the blood vessels, lowering the blood pressure. Hypotension may mask any cardioprotective effects due to reduction in coronary artery perfusion pressure, and would limit utility in treating myocardial ischemia. Therefore, the compounds of the present invention may be more optimal for cardioprotectives by virtue of their weak vasodilatation activity.

As illustrated above, the compounds of the present invention are so low in the vasorelaxant potencies that they are improved in the selectivity for heart protective function.

Experiment Example 8

Cardioprotective Activity in Isolated Ischemic Heart Models of Rats

In order to determine whether the compounds of the chemical formula 1 are protective for ischemic hearts in vitro, experiments determining the anti-ischemic effects of the compounds on isolated rat hearts were conducted as follows.

For all in vitro studies, isolated rat hearts were used according to the published methods after some modification [HJ Ring, *Arzneim.-Forsch./Drug Res.* 39 (II), 1535 (1989): T. Krzeminski, et al., *J. Pharmacological Methods*, 25, 95, (1991)]

Male Sprague-Dawley rats weighing 300-450 g were anesthetized with sodium pentobarbital (100 mg/kg, i.p.). The tail vein was injected with heparin (1,000 U/kg) and then the trachea was intubated. While rats were mechanically ventilated with a rodent ventilator (Model 7025, Ugobasile, Italy), their hearts were perfused in situ with oxygenated modified Krebs-Henseleit bicarbonate buffer (described herein) by retrograde aortic cannulation. The hearts were then excised and moved to a Langendorff apparatus (H.S.E., Germany), where they were perfused with oxygenated modified Krebs-Henseleit bicarbonate buffer containing (in mM) NaCl 116, NaHCO$_3$ 24.9, KCl 4.7, MgSO$_4$ 1.1, KH$_2$PO$_4$ 1.17, CaCl$_2$ 2.52, glucose 8.32 and pyruvate 2.0 at a constant perfusion pressure (85 mm Hg). A latex balloon filled with solvent (ethanol:water=1:1 (v/v)) and attached to a metal cannula was placed in the left ventricle through pulmonary vein and connected to a Isotec pressure transducer (H.S.E., Germany) for measurement of left ventricular pressure (LVP). The hearts were allowed to equilibrate for 15 min, at which time left ventricular end-diastolic pressure (EDP) was adjusted to 5 mm Hg and this balloon volume was maintained throughout the experiment. Then, baseline contractile function, heart rate (HR), and coronary flow (CF) (extracorporeal electromagnetic flow probe, Narco Bio-System, U.S.A.) were measured. Cardiac contractile function was calculated by subtracting LVEDP from LV peak systolic pressure (LVSP), yielding developed pressure (LVDP). Double product (DP), another important parameter for assessing cardiac performance, was calculated by multiplying HR by LVDP. Throughout the experiment, all these parameters were measured, and calculated before and 10 min after pretreatment with each compound and 30 min after the onset of reperfusion with buffer. Data on reperfusion DP were further expressed as the percentage to pretreatment DP.

After stabilization for 15 min, the hearts were pretreated for 10 min with respective drugs (10 μM, 0.04% DMSO) or vehicle (0.04% DMSO) before onset of global ischemia; test agents were administered directly into the oxygenator of the Langendorff apparatus immediately above the aortic root in a retrograde fashion as solutions in the perfusate. We then rendered the hearts globally ischemic by completely shutting off the perfusate for 30 min. Severity of ischemia was determined as the time to contracture (TTC, min) during global ischemia in which the first 5 mmHg increase in EDP was observed. Then, the hearts were reperfused and, 30 min later, contractile function (LVDP, DP) and cumulative reperfusion lactate dehydrogenase (LDH) release were measured. LDH was measured as a sensitive index for loss of cell viability with a kit supplied by Boerhinger Mannheim based on the technique of Wroblewski and LaDue [F. Wroblewski and J S. La Due, *Proc Soc Exp Biol Med* 90, 210, (1955)].

TABLE 10

Cardioprotective Effect of Compounds of Formula 1

| | Cardioprotection on Ischemic heart (μM) | | | |
|---|---|---|---|---|
| Test Drugs | LDVP × HR (%) | EDP (MmHg) | TTC (min) | LDH (U/g) |
| Vehicle | 23.0 | 43.4 | 20.3 | 29.9 |
| BMS-180448 | 67.6 | 16.5 | 27.8 | 17.2 |
| Example 1 | 55.7 | 24.0 | 28.0 | 10.7 |

In vehicle-treated group, reperfusion DP (LVDP×HR), a index for contractility function, was decreased to 23.0% of pretreatment DP, and EDP was increased to 43.3 mmHg from 5 mmHg, and TTC was 20.3 min, and reperfusion LDH release was 29.9 U/g as shown in the above table 10. In BMS-190448 treated group, reperfusion contractile function (DP, LVDP×HR) was 67.6% of pretreatment DP, which was significantly improved compared to vehicle treated group. EDP was 16.5 mmHg, significantly lower than control, and TTC was 27.8 min, prolonged than control, and reperfusion LDH release was 17.2 U/g, decreased than control. Then, in BMS-180448 treated group all parameters showed significant protective effect on ischemic heart. The compound of example 1 showed a good cardioprotective effect similar to BMS-180448, of which contractile function (LVDP×HR) was improved to 55.7% of pretreatment index, and EDP was 24.0 mmHg, and TTC was 28 min, and reperfusion LDH release was 10.7 U/g. However, because the compound of example 1 is 7 times lower vasorelaxant potency (IC$_{50}$=9.83 μM) than BMS-180448 does (IC$_{50}$=1.38 μM), it is superior to BMS-190448 in cardioselective antiischemic activity lower vasodilation potency than BMS-180448 (IC$_{50}$=1.38 μM). Consequently, the compounds of the present invention can be used for the treatment of ischemic heart diseases by virtue of their excellent selectivity and protective activity against ischemic cardiovascular diseases such as myocardial infarction, heart failure, and angina pectoris, etc.

Experiment Example 9

Cardioprotective Activity in Ischemic Heart Models of Rats

In order to determine whether the compounds of formula 1 are protective for ischemic hearts, experiments determining the anti-ischemic effects of the compounds on rats were conducted as follows.

Male rats (350-450 g, obtained from the Experimental Animal Team of the Korea Research Institute of Chemical Technology) were anesthetized by the intraperitoneal injection of pentobarbital at a dose of 75 mg/kg. After tracheotomy, the rats were rendered to respire artificially at a rate of 60/min with a stroke volume of 10 ml/kg. Cannulars were inserted into the fermoral vein and the fermoral artery and used for drug administration and blood pressure measurement, respectively.

In the ischemic myocardial injury models, the body temperature has an important influence on the results. To avoid the change in the body temperature, a body temperature measuring probe was inserted into the rectum of each rat and the body temperature was constantly kept at 37° C. with the aid of a homeothermic blanket control unit.

Afterwards, during testing, a continuous measurement was made of the mean arterial blood pressures and heart rates from the rats. For the measurement of the blood pressure, a pressure transducer (Statham P23XL, Grass Ins., MA, U.S.A.) was used. The heart rate was measured by a tachometer (ECG/RATE Coupler, Hugo Sachs Electronic, German) identified as Biotachometer. In addition, all of the changes occurring were continuously recorded through the Gould 2000 chart recorder (Graphtech Linearcorder W R 3310, Hugo Sachs Electronic).

The left coronary artery was occluded according to the Selye H. method as follows. The rats underwent a left thoracotomy operation for partial opening of the chest and the right-side chest was pressurized by the middle finger of the left hand to push the heart out. Immediately after the left anterior descending coronary artery hereinafter referred to as (LAD) was carefully stitched using a suture needle with 5-0 silk ligature, the heart was then repositioned in the thoracic cavity while both ends of the ligature were situated outside. The opposite ligature ends were passed through a PE tube (PE100, 2.5 cm) and allowed to stand loose for 20 min for stabilization. Via the cannula inserted into the femoral vein, vehicles or drugs were administered into the rats which were rendered to stand for 30 min in order to sufficiently elicit the efficacies of the drugs. BMS-180448 was used as a control drug and the i.v. administration dose was 0.3 mg/kg for all test drugs of interest and the control drug.

Next, the PE tube which had the doubled strands of the ligature passed therethrough was pushed toward the heart and then, set upright by tightly pulling end regions of the ligature with a hemostatic pincette while pressing the coronary artery. The PE tube was allowed to stand for 45 min for the occlusion of the coronary artery, followed by the removal of the hemostatic pincette and then, by the reperfusion for 90 min.

After the reocclusion of the coronary artery in accordance with the above procedure, the rats were administered with 2 ml of a 1% Evans blue through an intravenous route. Subsequently, an excess of pentobarbital was intravenously injected to kill the rats, after which the heat was removed and then, deprived of the right ventricle and both atria. The left ventricle was cut horizontally to the heart apex into 5 or 6 slices which were weighed. From the surface of each slice, images were input with the aid of a Hi-scope into a computer installed with an image analyzing program (Image Pro Plus). From the images input into the computer, the area of the normal blood stream tissue region which appeared blue in a computer monitor and the area which appeared colorless were measured. The percentage of the colorless area to the total area of each slice was calculated and multiplied by the weight of each slice to determine the area at risk (AAR) of each slice. The AAR obtained from each slice was summed for all slices and the total AAR was divided by the total weight of the left ventricle to yield % AAR, as shown in the following mathematical formula 3:

$AAR$ (%)=(summed $AAR$ for all slices)/(total weight of left ventricle)×100          [Mathematical Formula 3]

In addition, the heart slices were incubated for 15 min in 2,3,5-triphenyltetrazolium chloride (TTC) phosphate buffer (pH 7.4) at 37° C. and fixed for 20-24 hours in a 10% formalin solution. During this fixation, 2,3,5-triphenyltetrazolium chloride was reduced into formazan dye by the myocardial dehydrogenase and its cofactor NADH, so that the normal regions of the tissue were colored brick-red. In contrast, the infarct zones of the tissue were deficient in the dehydrogenase and its cofactor, so that no reduction occurred on the 2,3,5-triphenyltetrazolium, allowing the color to remain unchanged.

According to whether the tissue regions were colored by 2,3,5-triphenyltetrazolium, a measurement was made of the areas of the normal and infarct zones in each ventricle slice. The infarct zone area of each slice was summed for all slices and the resulting summed infarct zone area was divided by total AAR weight or total left ventricle weight to yield % IZ as shown in the following mathematical formula 4:

$IZ$ (%)=(summed infarct zone area)/(total left ventricle area)×100          [Mathematical Formula 4]

TABLE 11

Anti-Ischemic Effect of Compounds of Formula 1

| Compounds | Anti-ischemic effect Rat in vivo (0.3 mg/kg) | |
|---|---|---|
| | AAR/LV (%) | IZ/AAR (%) |
| Vehicle | 39.8 | 60.8 |
| BMS-180448 | 38.8 | 39.1 |
| Example 1 | 33.4 | 41.2 |

In the ischemic myocardium damage model of anesthetized rats, as seen in Table 4, the vehicle-treated group showed a myocardial infarction rate to area at risk (IZ/AAR) of 60.8%, which indicates a serious damage in the myocardial muscle. Being measured to be 39.1% in myocardial infarction rate, BMS-180448 showed noticeable anti-ischemic activity. When compared only in myocardial infarction rate, the compound of example 1 was similar to BMS-180448. However, because the compound of example 1 is remarkably lower in vasodilatation activity ($IC_{50}$=9.83 μM) than is BMS-180448 ($IC_{50}$=1.38 μM), it is superior to the conventional drug in cardioselective anti-ischemic activity. Further, the compounds of the present invention did not act to reduce the blood pressure in this experiment. Then, the compounds of the present invention can be used as a curative for the treatment of ischemic heart diseases by virtue of their excellent protective activity against ischemic cardiovascular diseases such as such as myocardial infarction, heart failure, and angina pectoris, etc.

Experimental Example 10

Acute Oral Toxicity Test in Rats

The test to confirm the toxicity of the compounds of formula 1 was carried out as follows.

In this test six-week old SPF SD rats were used with two rats assigned to each group. The compounds of examples 1-37 were suspended in 0.5% methyl cellulose, respectively, and administered orally in a single dose with 10 ml/kg/15 mL. After the administration, the animals were observed for clinical signs of toxicity or mortality and the body weight changes were measured. All survivors at the end of the observation period underwent laparotomy under ether anesthesia and the blood samples were taken from the abdominal aorta for hematological tests and biochemical analysis. After sacrificing the animals, autopsy was performed for macroscopic observation of the organs and tissues. Tissue samples of vital organs from macroscopic legion were removed and fixed in 10% neutral buffered formalin solution, then processed by standard procedures for histopathology and examined under light microscope. There were no significant changes in clinical symptoms, body weight and mortality. Also in hematology, serum chemistry parameters and macroscopic observation, no drug-related changes were observed. As a result all the compounds tested did not show toxicity in rats up to a dose of 10 mg/kg, and the lethal dose ($LD_{50}$) for oral administration was determined to be over 100 mg/kg in rats.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Formulation Examples

The pharmaceutical composition containing the compound of formula 1 as an active ingredient can be administered orally or parenterally. The method for preparation of a tablet for oral administration and the method for powders and capsules, and the method for an injection solution for parenteral administration are illustrated as the followings.

Formulation Example 1

Preparation of a Tablet (Direct Pressure)

The tablet containing 5 mg of the compound of formula 1 as an active ingredient was prepared as the followings. 5 mg of the compound was ground and passed through a sieve, and was mixed with 14.1 mg of lactose, 0.8 mg of crossphobidone USNF, and 0.1 mg of magnesium stearate. The resultant mixture was made into the tablet under pressure.

Formulation Example 2

Preparation of a Tablet

The tablet containing 5 mg of the compound of formula 1 as an active ingredient was prepared as the followings.

5 mg of the compound was passed through a sieve, and mixed with 16.0 mg of lactose, 4.0 mg of starch, and then an appropriate amount of polysorbate 80 (0.3 mg) solution was added. The resultant mixture was ground and passed through a sieve and then dried. Colloidal silicon dioxide and 2.0 mg of magnesium stearate were added and blended. The resultant mixture was made into the tablet by conventional method.

Formulation Example 3

Preparation of a Powder and Capsule 5 mg of the compound was passed through a sieve, and mixed with 14.8 mg of lactose, 10.0 mg of polyvinyl pyrrolidone, 0.2 mg of magnesium stearate. The resultant mixture was blended, and filled into a gelatin capsule (No. 5) using an appropriate instrument by conventional method.

Formulation Example 4

Preparation of an Injection Solution

The injection solution containing 100 mg of the compound of formula 1 as an active ingredient, and 180 mg of mannitol, 26 mg of $Na_2HPO_4.12H_2O$ in 2974 mg of distilled water, was prepared.

What is claimed is:

1. Benzopyran derivatives substituted with secondary amines including imidazole by the following formula 1, their stereochemical isomers and their pharmaceutically acceptable salts:

FORMULA 1

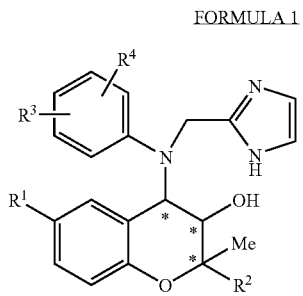

Wherein,
$R^1$ represents H, CN, $NO_2$ or $NH_2$,
$R^2$ represents

wherein $R^a$ represents straight or branched alkyl group of $C_1$-$C_4$,
$R_3$ and $R_4$ are independent each other and represent H, Cl, Br, F, alkyl group of $C_1$-$C_3$, $OR^b$, $CF_3$, $OCF_3$, $NO_2$, or $CO_2R^b$; $R^b$ represents H or alkyl group of $C_1$-$C_3$,
and * represents the chiral center.

2. Benzopyran derivatives substituted with secondary amines including imidazole, their stereochemical isomers and their pharmaceutically acceptable salts according to claim 1, wherein the compound of formula 1 is selected from the group consisting of:

1) (2S,3S,4R)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran;
2) (2S,3R,4S)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran;
3) (2R,3R,4S)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran;
4) (2R,3S,4R)-3,4-dihydro-2-dimethoxymethyl-3-hydroxy-2-methyl-6-nitro-4-[N-(4-chlorophenyl)-N-(1H-imidazol-2-ylmethyl)amino]-2H-1-benzopyran;
5) (2S,3S,4R)-3,4-dihydro-2-dimethoxymethyl-3-hydroxy-2-methyl-6-nitro-4-[N-(4-trifluoromethylphenyl)-N-(1H-imidazol-2-ylmethyl)amino]-2H-1-benzopyran;
6) (2S,3S,4R)-3,4-dihydro-2-dimethoxymethyl-3-hydroxy-2-methyl-6-nitro-4-[N-(4-methoxyphenyl)-N-(1H-imidazol-2-ylmethyl)amino]-2H-1-benzopyran;
7) (2S,3S,4R)-3,4-dihydro-2-dimethoxymethyl-3-hydroxy-2-methyl-6-nitro-4-[N-(4-trifluoromethoxyphenyl)-N-(1H-imidazol-2-ylmethyl)amino]-2H-1-benzopyran;
8) (2S,3S,4R)-3,4-dihydro-2-dimethoxymethyl-3-hydroxy-2-methyl-6-nitro-4-[N-(4-bromophenyl)-N-(1H-imidazol-2-ylmethyl)amino]-2H-1-benzopyran;
9) (2S,3S,4R)-3,4-dihydro-2-dimethoxymethyl-3-hydroxy-2-methyl-6-nitro-4-[N-(2,4-dimethylphenyl)-N-(1H-imidazol-2-ylmethyl)amino]-2H-1-benzopyran;
10) (2S,3S,4R)-3,4-dihydro-2-dimethoxymethyl-3-hydroxy-2-methyl-6-nitro-4-[N-(2-isopropylphenyl)-N-(1H-imidazol-2-ylmethyl)amino]-2H-1-benzopyran;
11) (2S,3S,4R)-3,4-dihydro-2-dimethoxymethyl-3-hydroxy-2-methyl-6-nitro-4-[N-(2,3-dimethylphenyl)-N-(1H-imidazol-2-ylmethyl)amino]-2H-1-benzopyran;
12) (2R,3R,4S)-3,4-dihydro-2-dimethoxymethyl-3-hydroxy-2-methyl-6-nitro-4-[N-(2,3-dimethylphenyl)-N-(1H-imidazol-2-ylmethyl)amino]-2H-1-benzopyran;
13) (2R,3R,4S)-3,4-dihydro-2-dimethoxymethyl-3-hydroxy-2-methyl-6-nitro-4-[N-(4-bromophenyl)-N-(1H-imidazol-2-ylmethyl)amino]-2H-1-benzopyran;
14) (2R,3R,4S)-3,4-dihydro-2-dimethoxymethyl-3-hydroxy-2-methyl-6-nitro-4-[N-(4-methoxyphenyl)-N-(1H-imidazol-2-ylmethyl)amino]-2H-1-benzopyran;
15) (2S,3S,4R)-3,4-dihydro-2-dimethoxymethyl-3-hydroxy-2-methyl-6-nitro-4-[N-(4-fluorophenyl)-N-(1H-imidazol-2-ylmethyl)amino]-2H-1-benzopyran;

16) (2S,3S,4R)-3,4-dihydro-2-dimethoxymethyl-3-hydroxy-2-methyl-6-nitro-4-[N-(2-methoxyphenyl)-N-(1H-imidazol-2-ylmethyl)amino]-2H-1-benzopyran;
17) (2R,3R,4S)-3,4-dihydro-2-dimethoxymethyl-3-hydroxy-2-methyl-6-nitro-4-[N-(2-isopropylphenyl)-N-(1H-imidazol-2-ylmethyl)amino]-2H-1-benzopyran;
18) (2R,3R,4S)-3,4-dihydro-2-dimethoxymethyl-3-hydroxy-2-methyl-6-nitro-4-[N-(2-methoxyphenyl)-N-(1H-imidazol-2-ylmethyl)amino]-2H-1-benzopyran;
19) (2R,3R,4S)-3,4-dihydro-2-dimethoxymethyl-3-hydroxy-2-methyl-6-nitro-4-[N-(3-chlorophenyl)-N-(1H-imidazol-2-ylmethyl)amino]-2H-1-benzopyran;
20) (2S,3S,4R)-3,4-dihydro-2-dimethoxymethyl-3-hydroxy-2-methyl-6-nitro-4-[N-(3-chlorophenyl)-N-(1H-imidazol-2-ylmethyl)amino]-2H-1-benzopyran;
21) (2R,3R,4S)-3,4-dihydro-2-dimethoxymethyl-3-hydroxy-2-methyl-6-nitro-4-[N-(4-trifluoromethoxyphenyl)-N-(1H-imidazol-2-ylmethyl)amino]-2H-1-benzopyran;
22) (2S,3S,4R)-6-cyano-3,4-dihydro-2-dimethoxymethyl-3-hydroxy-2-methyl-4-[N-(4-chlorophenyl)-N-(1H-imidazol-2-ylmethyl)amino]-2H-1-benzopyran;
23) (2R,3R,4S)-6-amino-3,4-dihydro-2-dimethoxymethyl-3-hydroxy-2-methyl-4-[N-(4-chlorophenyl)-N-(1H-imidazol-2-ylmethyl)amino]-2H-1-benzopyran;
24) (2S,3S,4R)-6-amino-3,4-dihydro-2-dimethoxymethyl-3-hydroxy-2-methyl-4-[N-(4-chlorophenyl)-N-(1H-imidazol-2-ylmethyl)amino]-2H-1-benzopyran;
25) (2S,3S,4R)-6-amino-3,4-dihydro-2-dimethoxymethyl-3-hydroxy-2-methyl-4-[N-(4-trifluoromethylphenyl)-N-(1H-imidazol-2-ylmethyl)amino]-2H-1-benzopyran;
26) (2R,3R,4S)-6-amino-3,4-dihydro-2-dimethoxymethyl-3-hydroxy-2-methyl-4-[N-(4-trifluoromethoxyphenyl)-N-(1H-imidazol-2-ylmethyl)amino]-2H-1-benzopyran;
27) (2R,3R,4S)-6-amino-3,4-dihydro-2-dimethoxymethyl-3-hydroxy-2-methyl-4-[N-(2,3-dimethylphenyl)-N-(1H-imidazol-2-ylmethyl)amino]-2H-1-benzopyran;
28) (2R,3R,4S)-6-amino-3,4-dihydro-2-dimethoxymethyl-3-hydroxy-2-methyl-4-[N-(4-methoxyphenyl)-N-(1H-imidazol-2-ylmethyl)amino]-2H-1-benzopyran;
29) (2R,3R,4S)-6-amino-3,4-dihydro-2-dimethoxymethyl-3-hydroxy-2-methyl-4-[N-(4-bromophenyl)-N-(1H-imidazol-2-ylmethyl)amino]-2H-1-benzopyran;
30) (2S,3S,4R)-6-amino-3,4-dihydro-2-dimethoxymethyl-3-hydroxy-2-methyl-4-[N-(2,3-dimethylphenyl)-N-(1H-imidazol-2-ylmethyl)amino]-2H-1-benzopyran;
31) (2S,3S,4R)-6-amino-3,4-dihydro-2-dimethoxymethyl-3-hydroxy-2-methyl-4-[N-(2-methoxyphenyl)-N-(1H-imidazol-2-ylmethyl)amino]-2H-1-benzopyran;
32) (2S,3S,4R)-6-amino-3,4-dihydro-2-dimethoxymethyl-3-hydroxy-2-methyl-4-[N-(4-methoxyphenyl)-N-(1H-imidazol-2-ylmethyl)amino]-2H-1-benzopyran;
33) (2S,3S,4R)-6-amino-3,4-dihydro-2-dimethoxymethyl-3-hydroxy-2-methyl-4-[N-(2,4-dimethylphenyl)-N-(1H-imidazol-2-ylmethyl)amino]-2H-1-benzopyran;
34) (2S,3S,4R)-6-amino-3,4-dihydro-2-dimethoxymethyl-3-hydroxy-2-methyl-4-[N-(2-isopropylphenyl)-N-(1H-imidazol-2-ylmethyl)amino]-2H-1-benzopyran;
35) (2S,3S,4R)-6-amino-3,4-dihydro-2-dimethoxymethyl-3-hydroxy-2-methyl-4-[N-(4-trifluoromethoxyphenyl)-N-(1H-imidazol-2-ylmethyl)amino]-2H-1-benzopyran;
36) (2S,3S,4R)-6-amino-3,4-dihydro-2-dimethoxymethyl-3-hydroxy-2-methyl-4-[N-(4-bromophenyl)-N-(1H-imidazol-2-ylmethyl)amino]-2H-1-benzopyran; and
37) (2S,3S,4R)-6-amino-3,4-dihydro-2-dimethoxymethyl-3-hydroxy-2-methyl-4-[N-(4-fluorophenyl)-N-(1H-imidazol-2-ylmethyl)amino]-2H-1-benzopyran.

3. A process for preparing the benzopyran derivatives substituted with secondary amines including imidazole of claim 1, comprising the step of reacting an epoxide compound (II) with a secondary amine compound including imidazole (III) in the presence of a metal salt in an reaction solvent to obtain a compound (I), as described in scheme 1:

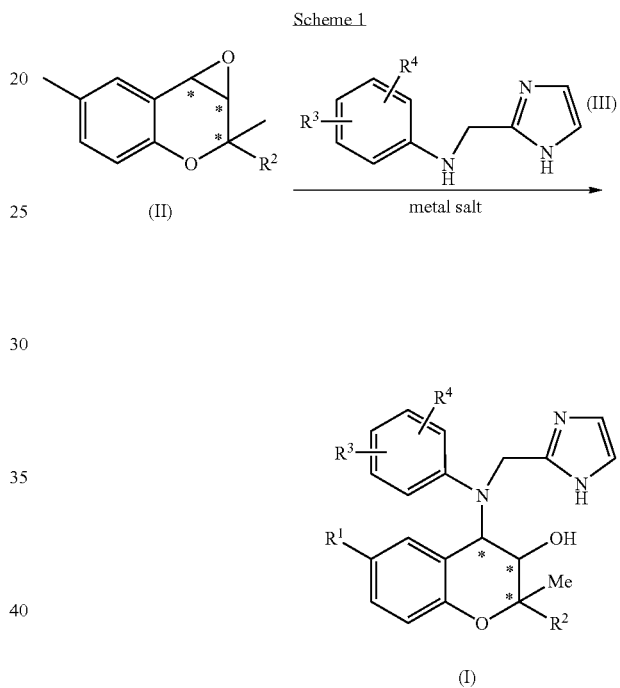

Wherein $R_1$, $R_2$, $R_3$, $R_4$ * and n are each defined as above claim 1, the metal salt is selected from the group consisting of $Mg(ClO_4)_2$, $CoCl_2$, $LiClO4_2$, $NaClO_4$, $CaCl_2$, $ZnCl_2$, $LiBF_4$ and $Zn(Tf)_2$, and the reaction solvent is selected from the group consisting of acetonitrile, tetrahydrofuran and dimethylformamide.

4. A process for for preparing the benzopyran derivatives substituted with secondary amines including imidazole of claim 1, comprising the step of
1) reduction of the nitro compounds (IV) by hydrogenation using metal catalysts such as platinum, palladium, palladium on carbon (Pd/C), Raney-nickel, etc. in a suitable solvent, to obtain the amino compound (V) as described in scheme 4, below; or
2) reduction of the nitro compounds (IV) using an reducing agent in the presence of $CuSO_4$, $Cu(OAc)_2$, $CoCl_2$, $SnCl_2$ or $NiCl_2$, to obtain the amino compound (V) as described in scheme 4, below:

Scheme 4
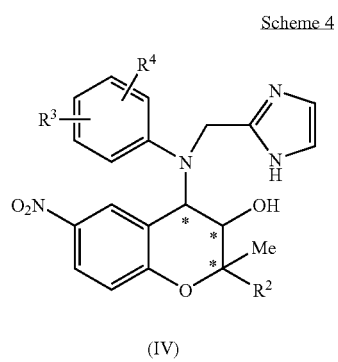
(IV)
reduction →
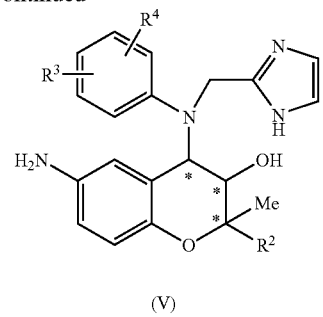
(V)
Wherein $R^2$, $R^3$, $R^4$ and * are each defined as above claim 1.
5. The process according to claim 4, wherein the reducing agent is $NaBH_4$.
* * * * *